United States Patent
Biswas et al.

(10) Patent No.: US 10,953,168 B2
(45) Date of Patent: Mar. 23, 2021

(54) METHOD AND APPARATUS TO MEASURE, AID AND CORRECT THE USE OF INHALERS

(71) Applicant: Cognita Labs, LLC, Houston, TX (US)

(72) Inventors: Rajoshi Biswas, Houston, TX (US); Gaurav P. Patel, Houston, TX (US); Ashutosh Sabharwal, Houston, TX (US)

(73) Assignee: Cognita Labs, LLC, Houston, TX (US)

( * ) Notice: Subject to any disclaimer, the term of this patent is extended or adjusted under 35 U.S.C. 154(b) by 1106 days.

(21) Appl. No.: 14/940,454

(22) Filed: Nov. 13, 2015

(65) Prior Publication Data

US 2016/0144141 A1    May 26, 2016

Related U.S. Application Data

(60) Provisional application No. 62/082,399, filed on Nov. 20, 2014.

(51) Int. Cl.
  *A61M 15/00* (2006.01)
  *G16H 20/10* (2018.01)
  (Continued)

(52) U.S. Cl.
  CPC .......... *A61M 15/009* (2013.01); *G16H 20/10* (2018.01); *G16H 20/40* (2018.01); *A61M 15/008* (2014.02);
  (Continued)

(58) Field of Classification Search
  CPC .............. A61M 15/00; A61M 15/0001; A61M 15/0065; A61M 15/0068; A61M 15/0071;
  (Continued)

(56) References Cited

U.S. PATENT DOCUMENTS 5,167,506 A    12/1992    Kilis et al.
5,333,106 A    7/1994    Lanpher et al.
(Continued)

FOREIGN PATENT DOCUMENTS

CA    2802197 A1    7/2014

OTHER PUBLICATIONS

Search Report and Written Opinion dated Jan. 29, 2016 in International Application No. PCT/US2015/060527.
(Continued)

*Primary Examiner* — LaToya M Louis
(74) *Attorney, Agent, or Firm* — Lombard & Geliebter LLP; Eric J. Huang

(57) ABSTRACT

A detachable cap for measuring usage of an inhaler includes a hollow receiving portion adapted to removably receive the inhaler. A vent is formed in a roof portion of the cap to allow airflow through the cap to the inhaler. An extension portion is provided for containing electronic components, including an electronic circuit provided in the extension portion, the electronic circuit including a controller coupled to a storage device and a power source. A pressure sensor is provided adjacent to the vent, the pressure sensor communicatively coupled to the controller and adapted to detect an air pressure within the cap. The controller is programmed to calculate an air flow rate through the cap based on the detected air pressure and to store the calculated air flow rate in the storage device.

20 Claims, 16 Drawing Sheets

(51) Int. Cl.
  G16H 20/40 (2018.01)
  A61M 16/00 (2006.01)
(52) U.S. Cl.
  CPC . *A61M 15/0016* (2014.02); *A61M 2016/0027* (2013.01); *A61M 2205/0233* (2013.01); *A61M 2205/18* (2013.01); *A61M 2205/332* (2013.01); *A61M 2205/3331* (2013.01); *A61M 2205/3553* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/583* (2013.01)
(58) Field of Classification Search
  CPC ............ A61M 15/008; A61M 15/0081; A61M 15/0083; A61M 2205/332; A61M 2205/3334
  See application file for complete search history.

(56) References Cited

U.S. PATENT DOCUMENTS

| | | | |
|---|---|---|---|
| 5,363,842 | A | 11/1994 | Mishelevich et al. |
| 6,358,058 | B1 | 3/2002 | Strupat et al. |
| 7,219,664 | B2 | 5/2007 | Ruckdeschel et al. |
| 8,342,172 | B2 | 1/2013 | Levy et al. |
| 8,464,707 | B2 | 6/2013 | Jongejan et al. |
| 8,807,131 | B1 | 8/2014 | Tunnell et al. |
| 9,526,858 | B2* | 12/2016 | Zuyderhoudt ...... A61M 15/009 |
| 2006/0237001 | A1* | 10/2006 | Stangl .................. A61M 11/005 128/200.23 |
| 2006/0254581 | A1 | 11/2006 | Genova et al. |
| 2008/0156321 | A1 | 7/2008 | Bowman et al. |
| 2008/0178872 | A1 | 7/2008 | Genova et al. |
| 2008/0230057 | A1 | 9/2008 | Sutherland |
| 2009/0194104 | A1 | 8/2009 | Van Sickle |
| 2012/0055472 | A1 | 3/2012 | Brunnberg et al. |
| 2012/0240925 | A1 | 9/2012 | Kaar et al. |
| 2014/0007867 | A1 | 1/2014 | Bruin et al. |
| 2014/0182584 | A1 | 7/2014 | Sutherland et al. |
| 2014/0216444 | A1 | 8/2014 | Shtram et al. |
| 2014/0352692 | A1 | 12/2014 | Mayer |
| 2015/0061867 | A1 | 3/2015 | Engelhard et al. |
| 2015/0100335 | A1 | 4/2015 | Englehard et al. |
| 2015/0208729 | A1* | 7/2015 | Monsees ............... H02J 7/0044 131/329 |
| 2017/0290527 | A1* | 10/2017 | Morrison .......... A61M 16/0051 |

OTHER PUBLICATIONS

"Propeller Health: Tools to Track, Manage, and Research Asthma and COPD", California Healthcare Foundation, Sep. 2013.
Rajoshi Biswas et al., "Demonstration Paper: AsthmaGuru: A Framework to Improve Adherence to Asthma Medication", Wireless Health '13, 2013.
R.W. Costello et al., "Assessing True Inhaler Adherence in COPD Patients", Abstract, Am J Respir Crit Care Med, vol. 187, 2013.
Prabhakaran L, "The use of text messaging to improve asthma control: a pilot study using the mobile phone short messaging service (SMS)", J Telemed Telecare, vol. 16(5), 2010, Abstract.
Fact Sheet Chronic Obstructive Pulmonary Disease (COPD), National Institutes of Health, http://report.nih.gov/NIHfactsheets/ViewFactSheet. aspx?csid=77, Oct. 2010.
Cynthia S. Rand et al., "Metered-Dose Inhaler Adherence in a Clinical Trial", Am Rev Respir Dis, vol. 146, pp. 1559-1564, 1992.
M. Molimard, M.D., Ph.D. et al, "Assessment of Handling of Inhaler Devices in Real Life: An Observational Study in 3811 Patients in Primary Care", Journal of Aerosol Medicine, vol. 16, No. 3, pp. 249-254, 2003.
Vicente Plaza et al., "Medical Personnel and Patient Skill in the Use of Metered Dose Inhalers: A Multicentric Study", Respiration, vol. 65, pp. 195-198, 1998.
Arlette E. Hesselink et al., "Determinants of an incorrect inhalation technique in patients with asthma or COPD", Scand J Prim Health Care, vol. 19, pp. 255-260, 2001.
Arvid W.A. Kamps, MD, et al., "Poor Inhalation Technique, Even After Inhalation Instructions, in Children With Asthma", Pediatric Pulmonology, vol. 29, pp. 39-42, 2000.
J Bourbeau et al., "Patient adherence in COPD", Thorax, vol. 63, pp. 831-838, 2008.
J Vestbo et al, "Adherence to inhaled therapy, mortality and hospital admission in COPD", Thorax, vol. 64, pp. 939-943, 2009.
R. Pauwels et al., "Airway deposition and airway effects of antiasthma drugs delivered from metered-dose inhalers", Eur Respir J, vol. 10, pp. 2127-2138, 1997.
Andrea S. Melani et al., "Inhaler mishandling remains common in real life and is associated with reduced disease control", Respiratory Medicine, vol. 105, pp. 930-938, 2011.
Marlene E.A.C. Broeders, MD, et al., "Inhalation Profiles in Asthmatics and Copd Patients: Reproducibility and Effect of Instruction", Journal of Aerosol Medicine, vol. 16, No. 2, pp. 131-141, 2003.
H. Pinnock et al., "Understanding the potential role of mobile phone-based monitoring on asthma self-management: qualitative study", Clinical and Experimental Allergy, vol. 37, pp. 794-802, 2007.
Katie M Buston et al., "Non-compliance amongst adolescents with asthma: listening to what they tell us about self-management", Family Practice, vol. 17, No. 2, pp. 134-138, 2000.
William M. Vollmer, PhD et al., "Use and impact of an Automated Telephone Outreach System for Asthma in a Managed Care Setting", The American Journal of Managed Care, vol. 12, No. 12, pp. 725-733, Dec. 2006.
K.C. Ringsberg et al., "Education of adult patients at an 'asthma school': effects on quality of life, knowledge and need for nursing", Eur Respir J, vol. 3, pp. 33-37, 1990.
Henry A. Wojtczak, Md et al., "Understanding the relationship among pharmacoadherence measures, asthma control test scores, and office-based spirometry", Ann Allergy Asthma Immunol, vol. 109, pp. 103-107, 2012.
Kristin A. Riekert et al., "Electronic Monitoring of Medication Adherence: When Is High-Tech Best?", Journal of Clinical Psychology in Medical Settings, vol. 9, No. 1, pp. 25-34, Mar. 2002.
S. Hamid et al., "Single centre open study to compare patient recording of PRN salbutamol use on a daily diary card with actual use as recorded by the MDI compliance monitor", Respiratory Medicine, vol. 92, pp. 1188-1190, 1998.
Andrew G. Weinstein, MD, "Should patients with persistent severe asthma be monitored for medication adherence", Annals of Allergy, Asthma & Immunology, vol. 94, pp. 251-257, Feb. 2005.
Sundeep Salvi et al., "India Needs a National COPD Prevention and Control Programme", Supplement to JAPI, vol. 60, pp. 5-7, Feb. 2012.
Bruce Bender, PhD et al, "Measurement of children's asthma medication adherence by self report, mother report, canister weight, and Doser CT", Annals of Allergy, Asthma, & Immunology, vol. 85, pp. 416-421, Nov. 2000.
State of the Air 2013, American Lung Association, http://www.stateoftheair.org, pp. 1-175, 2013.
Sundeep Salvi et al., "Is Exposure to Biomass Smoke the Biggest Risk Factor for COPD Globally?" CHEST, vol. 138, No. 1, Jul. 2010, pp. 3-6.
Alvaro Cruz, "Global Surveillance, prevention and control of Chronic Respiratory Diseases a comprehensive approach," World Health Organization, pp. 1-146, 2007.
Chronic Obstructive Pulmonary Disease (COPD), American Lung Association Lung Disease Data: 2008, American Lung Association, 2008, http://www.lung.org/assets/documents/publications/lung-disease-data/ldd08-chapters/LDD-08-COPD.pdf, pp. 41-53.
G. M. Cochrane et al., "Compliance in asthma", Respiratory Medicine, 1999, vol. 93, pp. 763-769.
Inhaler technique in adults with asthma or COPD, National Asthma Council Australia, 2008, http://www.nationalasthma.org.au/uploads/publication/inhaler-technique-in-adults-with-asthma-orcopd.pdf, pp. 1-9.

(56) References Cited

OTHER PUBLICATIONS

Toby GD Capstick et al., "Inhaler technique and training in people with chronic obstructive pulmonary disease and asthma", Expert Rev. Respir. Med. 6(1), 2012, pp. 91-103.
Mitch Posada, "Propeller Health's journey to address COPD and Asthma via a Connected Device", On the Path . . . Healthcare Software Development Blog, http://blog.pathfindersoftware.com/blog/david-van-sickle-detailing-propeller-healths-journey-to-address-copd-and-asthma, Jun. 23, 2014.
Thomas Charles et al., "An audiovisual reminder function improves adherence with inhaled corticosteroid therapy in asthma", J Allergy Clin Immunol, Apr. 2007, pp. 811-816.
Alison Hardwell et al., "Technique training does not improve the ability of most patients to use pressurised metered-dose inhalers (pMDIs)", Primary Care Respiratory Journal, (2011), 20(1), pp. 92-96.
Federico Lavorini et al., "The ADMIT series—Issues in Inhalation Therapy. 6) Training tools for inhalation devices", Primary Care Respiratory Journal: Journal of the General Practice Airways Group, Nov. 2010.
James B Fink et al., "Problems With Inhaler Use: A Call for Improved Clinician and Patient Education", Respiratory Care, Sep. 2005, vol. 50, No. 10, pp. 1360-1375.
B.L. Laube et al., "What the pulmonary specialist should know about the new inhalation therapies", European Respiratory Journal, 2011, vol. 37, pp. 1308-1331.
International Preliminary Report on Patentability and Written Opinion dated Jun. 1, 2017 in International Application No. PCT/US2015/060527.

\* cited by examiner

METHOD AND APPARATUS TO MEASURE, AID AND CORRECT THE USE OF INHALERS

This application claims priority under 35 U.S.C. § 119 to U.S. Provisional Patent Application No. 62/082,399, filed on Nov. 20, 2014, which is incorporated by reference herein in its entirety.

FIELD OF THE INVENTION

The present invention relates generally to (i) medication adherence to a prescribed dosage routine, and (ii) inhaler competence in correctly using metered dose inhalers.

BACKGROUND OF THE INVENTION

The treatment for asthma and chronic obstructive pulmonary disease (COPD) patients consists of a combination of control and rescue medications. The control (sometimes also referred to as maintenance) medication is often taken daily (one or more times in a day, as prescribed by the patient's physician) to keep the disease progression and symptoms under control, and avoid reaction towards triggers that cause exacerbations (e.g. Asthma attacks). The rescue (also sometimes referred to as emergency) medication is often used during an exacerbation. The rescue medication provides quick relief in the case of exacerbation, and can have higher efficacy if the patient is compliant with the daily control medication regime.

Thus, it is generally considered important that patients maintain their prescribed medication regimen for better health outcomes. There is strong clinical evidence that regular use of the control medication minimizes long-term damage to the lungs and results in improved health outcomes for the patients. Additionally, regular and correct use of asthma inhaler medication leads to well-controlled asthma, reflected as low incidences of asthma-related exacerbations, hospitalizations, and deaths.

Metered Dose Inhaler (MDI) and Dry Powdered Inhaler (DPI) are the two most common mechanisms to deliver medicine for patients suffering from Asthma and COPD and can be used for dispensing either control or rescue medication. Patients are often provided both the written guidelines and training on the correct use of their prescribed inhaler. Despite well-known methods to manage Asthma and COPD, the two big challenges for patients in disease management are as follows. First, many patients do not display correct technique in using their prescribed inhaler. Incorrect technique leads to reduced deposition of medication. Second, many patients do not take their medications as frequently as prescribed. This can lead to medication consumption incommensurate with prescribed dosage.

A challenge in using an inhaler is that many patients use the inhaler with incorrect technique. The incorrect use is despite the fact that step-by-step standardized guidelines have been established for inhalers, and patients are often coached by their physicians or equivalent healthcare professional. As an example, the guidelines may include the following steps for MDIs:

1. Shake inhaler (for inhaler medications with suspensions only).
2. Breathe out before actuating the inhaler.
3. Place mouthpiece between lips and over tongue keeping the inhaler upright.
4. Actuate the inhaler while breathing in through the mouth deeply.
5. Continue to breathe in slowly for at least 4 seconds.
6. Hold breath for 10 s or as long as possible and then breathe out.

The number of steps and methods to use the inhaler can vary from one inhaler to another, or from one inhaler-use guideline to another. The main point of the example is to illustrate that inhaler use has many steps, and some steps can be interpreted differently due to lack of precision in their description. For example, breathing deeply (in Step 4 of the above example) or slowly (in Step 5 of the above example) can be interpreted differently by different inhaler users.

The above guidelines seek to ensure that a sufficient amount of the medication inhaled through the mouth reaches the lungs, while minimizing the amount deposited in the mouth or throat area. For example, Step 1 of shaking the inhaler prepares the solution canister to release the recommended concentration of medication on actuation. Similarly, a slow continuous inspiration and inhaler actuation at the right time results in the medication depositing inside the lungs rather than inside the mouth and throat area.

However, due to the subjective nature of some of the steps in guidelines, e.g. breathing deeply and slowly, it can be a difficult task for some patients to gauge how well they adhere to the ideal inhaler usage technique. In medical literature, this problem is sometimes referred to as lack of inhaler competence. In fact, it can also be challenging for some healthcare professionals to gauge whether the patients are correctly using the inhaler even when the patients demonstrate their technique in front of them. One reason for the challenge to correctly use the inhaler is that the inhalers often do not come equipped with features which can inform whether they are using their inhaler correctly or not.

The second major challenge faced by patients is poor adherence to the prescribed control or rescue medication regimen. For example, there are cases that the control medication should be taken by Asthma and COPD patients at least once daily, in order to suppress their symptoms. Good adherence to control medication results in lower sensitivity towards exacerbation triggers. However, many patients find it difficult to maintain regularity in their medication. The primary reason is forgetfulness in taking the prescribed dosage with the prescribed regularity and difficulty in keeping track of their total medication intake. For example, patients often find it hard to remember the amount of medication left in the inhaler, especially for those inhalers that do not come equipped with dose counter.

The current MDI inhalers may not be straightforward to use for some patients. As described in the example above, some guidelines for inhaler use include six steps involved in operating the MDI. But while using MDIs, the patients do not have quantitative measurement of their inhaler usage technique, real-time guidance about usage technique, or evaluation of the correctness of the technique. Patients are generally trained to correctly use the inhalers by nurses and physicians, often by practicing with training devices that monitor usage techniques. The inhaler training devices are electronic devices that measure breathing patterns and are generally tabletop devices with an attached medication canister, as they are not compatible with off the shelf MDIs. But most patients do not get any feedback or insight from their regular MDIs and may forget the exact technique after the training, continuing to use their inhalers incorrectly. Some inhalers, known as breath-actuated inhalers, have an automated medication dispenser based on inhalation flow rate to assist with the timing of actuation. However, there is little or no feedback provided about the accuracy of the rest of the inhaler usage technique.

Additionally, inhalers are often prescribed with a spacer. A spacer is a hollow plastic or metallic tube attached with the inhaler to increase the ease of use and efficacy of administering medication. Spacers are anti-static or coated with anti-static material to avoid medication sticking to its walls and have a one-way valve to ensure the medication is delivered only during an inspiration. The inhaler fits to the spacer in an upright position taking care of the right orientation required for inhaler usage.

A spacer acts as a holding chamber to assist with medication intake. When the inhaler releases the medication into the spacer, it is suspended inside the chamber providing patients longer time to breathe in the medicine. Therefore, the coordination required for actuation is easier for the patient to learn.

However, the spacer does not provide feedback or monitor the inhaler use, e.g. number of times the inhaler was shaken, inspiration flow rate or duration of time the breath is held. Previous research studies have shown that patients incorrectly use the MDI even with a spacer, for example by breathing in too quickly, too fast or not at all. Spacers are also considered bulky by some patients, and thus some patients avoid carrying their spacers due to inconvenience of transporting them. Therefore, a spacer remains an incomplete solution for many patients in addressing the challenge of monitoring usage and correcting technique.

To address the challenge of non-regularity of inhaler use, many current inhalers, both MDI and DPI, are mechanical devices sometimes built with an internal dose counter for record keeping. The dose counter lets patients know when the inhaler is empty so they can re-fill their prescription, and in some cases, also gives physicians the record of the number of times the inhaler is pressed. However, merely counting dosage does not accurately represent adherence. Many studies have shown that patients sometimes dump the contents of the inhalers just before their visit to the doctor or pharmacist (spraying inhalers away from their mouth), thus falsifying their inhaled dose counts. Physicians are, therefore, oblivious to the patient's actual adherence to inhaler medication.

Moreover, there have been numerous efforts in the past for inhaler medication reminder systems, like interventions through nurses and caregivers, manual and electronic systems for dosage reminder and tracking. However, the effectiveness of reminder systems was short term due to limitations of scale and duration of the research studies. Although manual diaries are still widely used for keeping a record of the patient's daily medication dosage, a number of smartphone-based applications are emerging for making the above task more automated.

There are some small, add-on electronic monitoring devices available to monitor adherence. The electronic monitors consist of sensors to detect when and where the inhaler is pressed, and can remind the patients to take their medication. Time and location stamping of inhaler dosage provides doctors with more accurate information about inhaler adherence. Many of these add-on devices can communicate with smartphones to view and share the adherence records with their doctors. The reminder systems of the dosage monitors are alarms preset by the users according to their prescription. However, the currently available electronic inhaler monitors face two major disadvantages. First, none of these devices actually monitor whether the patient inhaled the medication or dumped it outside. The devices are incapable of evaluating the quality of the dosage, that is, whether the patients used the inhaler incorrectly. The time and location of inhaler usage only reflect adherence to inhaler actuation and not actual inhalation of the inhaler medication. Hence, the inhaler adherence records obtained from the monitors are incomplete and potentially unreliable. Thus, there is a need to develop smarter adherence systems to track the inhaler usage verifiably, learn mistakes made by patients while taking MDI or DPI dosage and remind the patients to correct their errors in inhaler usage, e.g. the next time they use the inhaler.

Second, the primitive nature of the dosage reminder systems often leads to patients ignoring the alarms and forgetting to take their medication. Ideally, the reminder system should understand the user context and then adjust the reminder system accordingly. However, current reminder systems do not have any method to understand user context. It is, therefore, necessary to develop smarter reminder systems that provide notifications or alarms at the ideal moment for the patient to take the medication.

SUMMARY OF THE INVENTION

In an embodiment, the invention provides a detachable cap for measuring usage of an inhaler, where the cap includes a hollow receiving portion adapted to removably receive the inhaler. A vent is formed in a roof portion of the cap to allow airflow through the cap to the inhaler. An extension portion is provided for containing electronic components, including an electronic circuit provided in the extension portion, the electronic circuit including a controller coupled to a storage device and a power source. A pressure sensor is provided adjacent to the vent, the pressure sensor communicatively coupled to the controller and adapted to detect an air pressure within the cap. The controller is programmed to calculate an air flow rate through the cap based on the detected air pressure and to store the calculated air flow rate in the storage device.

In another embodiment, the invention provides a method of detecting usage of an inhaler, the method including providing a detachable cap adapted to removably receive the inhaler. The cap includes a vent formed in a roof portion of the cap to allow airflow through the cap to the inhaler, an extension portion for containing electronic components including an electronic circuit having a controller coupled to a storage device and a power source, a pressure sensor adjacent to the vent, the pressure sensor communicatively coupled to the controller and adapted to detect an air pressure within the cap. The method further includes detecting the air pressure within the cap with the pressure sensor, calculating, with the controller, an air flow rate through the vent based upon the detected air pressure, and storing the calculated air flow rate in the storage device.

In another embodiment, the invention provides a system for providing feedback to a user regarding usage of an inhaler, the system including an electronic device that includes a non-transitory computer-readable medium comprising instructions stored thereon. When the instructions are executed on a processor of the electronic device, they perform the steps of displaying a window on a graphical user interface on the electronic device, continuously monitoring parameters of actual inhaler usage when the inhaler is used, comparing the parameters of actual inhaler usage with a predetermined range of parameters that define recommended inhaler usage, determining whether the inhaler usage is recommended inhaler usage based on the comparison of the parameters of actual inhaler usage with the predetermined range of parameters, and providing feedback to the user by displaying graphics on the window on the graphical user interface related to the comparison of the parameters of actual inhaler usage with the predetermined range of parameters. When the inhaler usage is not recommended inhaler usage, the feedback to the user provides instructions for improving the inhaler usage.

In another embodiment, the invention provides a computer-implemented method for providing feedback to a user regarding usage of an inhaler. The method includes displaying a window on a graphical user interface on an electronic device, continuously monitoring parameters of actual inhaler usage when the inhaler is used, comparing the parameters of actual inhaler usage with a predetermined range of parameters that define recommended inhaler usage, determining whether the inhaler usage is recommended inhaler usage based on the comparison of the parameters of actual inhaler usage with the predetermined range of parameters, and providing feedback to the user by displaying graphics on the window on the graphical user interface related to the comparison of the parameters of actual inhaler usage with the predetermined range of parameters. When the inhaler usage is not recommended inhaler usage, the feedback to the user provides instructions for improving the inhaler usage.

The technology described in this application facilitates collection of detailed parameters about the use of metered dose or dry powder inhalers, and potential use of the parameters for one of many possible purposes. An attachment is equipped with many sensors to measure different aspects of inhaler usage technique. The sensors can measure any combination of the following exemplary parameters: pre-intake shaking, number of inhaler actuation, force applied for actuation, breathing flow-rate, temperature and humidity, time, date and place of actuation, and duration of breath hold after the medication inhalation. The measured parameters can be used for one of many possible purposes, including but not limited to, providing feedback to patient or medical practitioner or both, about the inhaler usage. The feedback can be provided in real-time as the patient is using the inhaler or after the inhaler has been used.

In one exemplary embodiment, a comprehensive inhaler management system includes an attachment to off-the-shelf MDI inhalers coupled with a smartphone app, combined with a potentially cloud-based data storage and analytics. The embodiment is an electronic add-on device for the inhaler, built in a small form factor, e.g. as a cap on an existing MDI. The sensors in the MDI attachment quantitatively measure the inhaler technique and its correctness, as well as provide real-time feedback and guidance while the patient uses the MDI. The sensors also detect the timestamp, location of MDI dosage and MDI use by a person, to accurately track and improve adherence to medication regime. In addition, the MDI attachment communicates with patient's or physician's (or both) smartphones, tablets, computers, and/or home/work WiFi networks or cellular networks, for easy data viewing, sharing and storage. The smartphone application ("app") can also connect to a cloud for storage, analysis and communicating with a healthcare provider and/or pharmacy for pre-emptive refills. The attachment device can also connect to cloud without a smartphone through a communication (Bluetooth™/WiFi) hub at home or work. The hub itself can be portable and be carried by the user. It is also possible to have multiple hubs at home or at work or both, so that the MDI attachment has higher chance to find an available hub. Further, in absence of any such communication mode (smartphones or tablets or computers or hub), the device can simply store data in its internal storage, to be transferred to the cloud later in-clinic. The inhaler use data can also be communicated to electronic health records. That is, the inhaler usage data can be further used to provide additional services to the patient to make it easier to stay adherent to the prescribed regimen.

The shape of the inhaler attachment can be in the form of a cap, but is not limited to be such. The attachment will snuggly fit the target MDIs, with a vent on the top as a passage for airflow through the attachment and MDI. Design of the MDI cap and vent ensures that it does not increase the resistance of the inhaler beyond the acceptable limits. The length and shape of the cap is designed to facilitate a tight fit on the MDI that makes the airflow through the setup laminar and allow measurement of flow rates. Moreover, the cap may be designed such that its operation is either completely or partially automated, depending on the design goal for the end products. The cap may have an auto on-off feature, which, as an example, can be implemented using a capacitive touch sensor. In this example, the capacitive touch sensor, located on the top of the inhaler, detects human touch and turns the device on. Algorithms can differentiate between accidental touch or actual inhaler use using flow-sensor and accelerometer data. The auto on-off feature can potentially be used with other sensors or combination of sensors, along with associated algorithms, that can estimate user intent and turn the cap on or switch it off automatically.

In another embodiment, the inhaler cap can provide real-time coaching to the inhaler users by giving feedback about their inhaler usage technique, while they use the MDI. The feedback can be provided in the form of audio, using a built-in small speaker or a buzzer. The feedback can also be provided in the form of visual cues, using built-in light emitting diodes (LED). Furthermore, haptic feedback can be provided in the form of small vibrations, such as that available in smartphones. Audio, visual and haptic cues can also be combined. The cues can also be provided via an app on the user's smartphone, and can be potentially combined with the audio or visual cues by the inhaler cap. An example use of the cues can be to inform the user on changing their flow rate during their inhaler usage. Another example use of the cues is to remind the users to hold their breath for a certain amount of time, and possibly providing a cue for that duration of time. FIG. 1 provides an example use of an inhaler attachment coupled with a smartphone app. The example in FIG. 1 is only one of the many possible uses, and many different implementations of the attachment are possible where a smartphone app may or may not be used as elaborated above in the different embodiments. The feedback can be implemented directly on the inhaler attachment, or a smartphone, tablet, personal computer or laptop.

In another embodiment, the inhaler cap can be used as a teaching tool by the healthcare professionals to teach their patients or by patients themselves. Using the built-in sensors in the inhaler cap, data about a patient's inhaler usage can be collected, and shared with the user or the healthcare professionals or both. The data can then be used to help correct the MDI usage technique in future use. The data can also be used to track the improvement in inhaler use over time.

In another embodiment, the cap is used to verify the level of patient's adherence to the prescribed regimen. Since the cap can measure many different types of inhaler usage parameters, like flow-rate, temperature and humidity of the breath, the data can be used as a method to verify if the patient actually took medication as prescribed, and did not intentionally/accidentally dump the medicine. This data can be used by caregivers, like parents, guardians, helpers, healthcare workers or physicians, to learn about the medication adherence of the patients.

In another embodiment, the collected data from the inhaler, that can be any combination or subset of the data described in above embodiments, can be used by healthcare professionals to understand the usage of their one or more patients. This information can be used in a myriad of ways. For example, the data could indicate methods to improve the clinical practice. If it is known that a patient is having a difficult time operating the inhaler, then the healthcare providers can dedicate additional time to coach the patient. Similarly, if a patient is unable to use the inhaler regularly, then the clinical staff can discuss the reasons behind irregular use and develop methods to improve regularity of usage. The collected information of patient's MDI usage technique over time can also be used to build a unique personal profile for each patient. The personal profile can be analyzed further to give personalized feedback and training to improve MDI usage, e.g., using the knowledge of strategies which have been successful with other patients with a similar profile.

In another embodiment, the physician or healthcare professional can use the data that can be any combination or subset of the data described in above embodiments, to adjust the prescribed inhaler medicine. For example, if a patient's health outcomes remain inadequate despite demonstrating correct technique and regular use, the physician can change the prescription. The physician can also prescribe the appropriate type of inhaler (MDI, DPI or other, such as soft-mist inhalers) based on the patient's technique of using the inhaler as recorded by embodiments of the invention.

In another embodiment, the mobile, desktop or web app developed for disease management with the inhaler attachment is intelligently designed to provide 'smart' reminders to the patient. These reminders are of different types: (i) reminder to take the dose at the correct time, (ii) reminder to refill the inhaler before it is completely exhausted and (iii) reminder to carry the inhaler as the patient leaves a current location like home or work, so that the inhaler is available for use during travel. The app monitors inhaler attachment & smartphone context, by measuring patterns in inhaler use. The context parameters can include (but not limited to) a set of common times to take the inhaler as measured by the cap hardware, physical location of inhaler use and the patient's motion data. Patient/user's physical location and motion data can be captured by a smartphone's GPS and accelerometer sensors respectively. The context parameters can be used to calculate the good times, locations and method (audio or visual reminders) to remind the patient to carry/use/refill the inhaler. For example, a smartphone application can remind the patient to carry the inhaler when he/she leaves home. The smartphone application can implement geo-fencing to keep track of a patient entering or leaving certain locations such as home, and combine inhaler dosage timestamp and count information to give accurate reminder to carry/take dose. The advanced reminder system can be more effective, adapts to patient's lifestyle, and can result in higher patient response to the desired actions.

BRIEF DESCRIPTION OF THE DRAWINGS

The accompanying drawings, which are incorporated herein and constitute part of this specification, illustrate the presently preferred embodiments of the invention, and together with the general description given above and the detailed description given below, serve to explain features of the invention.

DETAILED DESCRIPTION OF THE PREFERRED EMBODIMENTS

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a particular system. However, the embodiments to be discussed next are not limited to the particular discussed system but may be applied to other existing inhaler delivery mechanisms.

Reference throughout the specification to "one embodiment" or "an embodiment" means that a particular feature, structure, or characteristic described in connection with an embodiment is included in at least one embodiment of the present invention. Thus, the appearance of the phrases "in one embodiment" or "in an embodiment" in various places throughout the specification are not necessarily all referring to the same embodiment. Further, the particular features, structures or characteristics may be combined in any suitable manner in one or more embodiments.

Figures 12A, 12B:
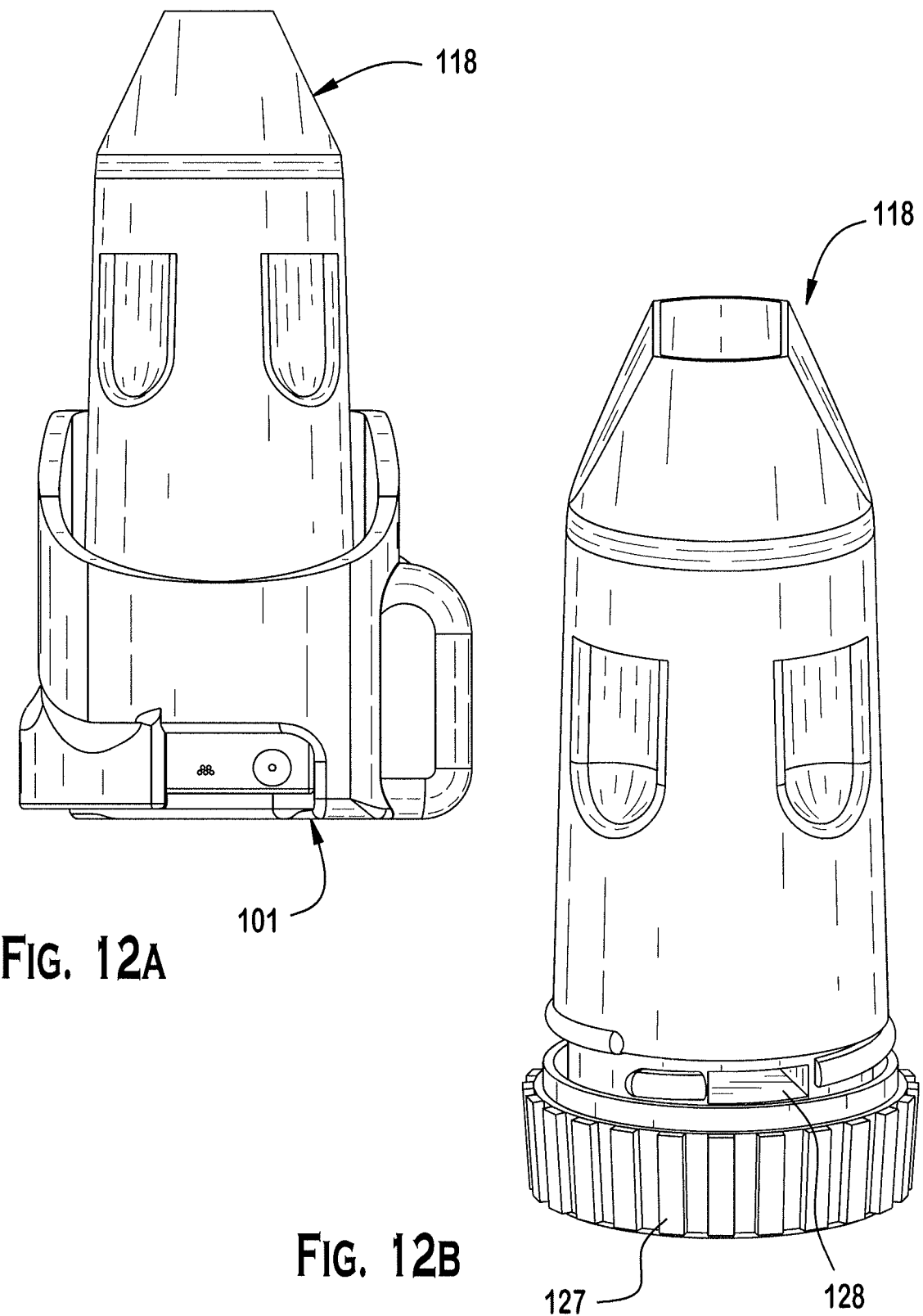
FIG. 12A is a front view of an inhaler management system according to an embodiment.
FIG. 12B is a perspective view of an inhaler as shown in the inhaler management system in FIG. 12A.
Figure 13:
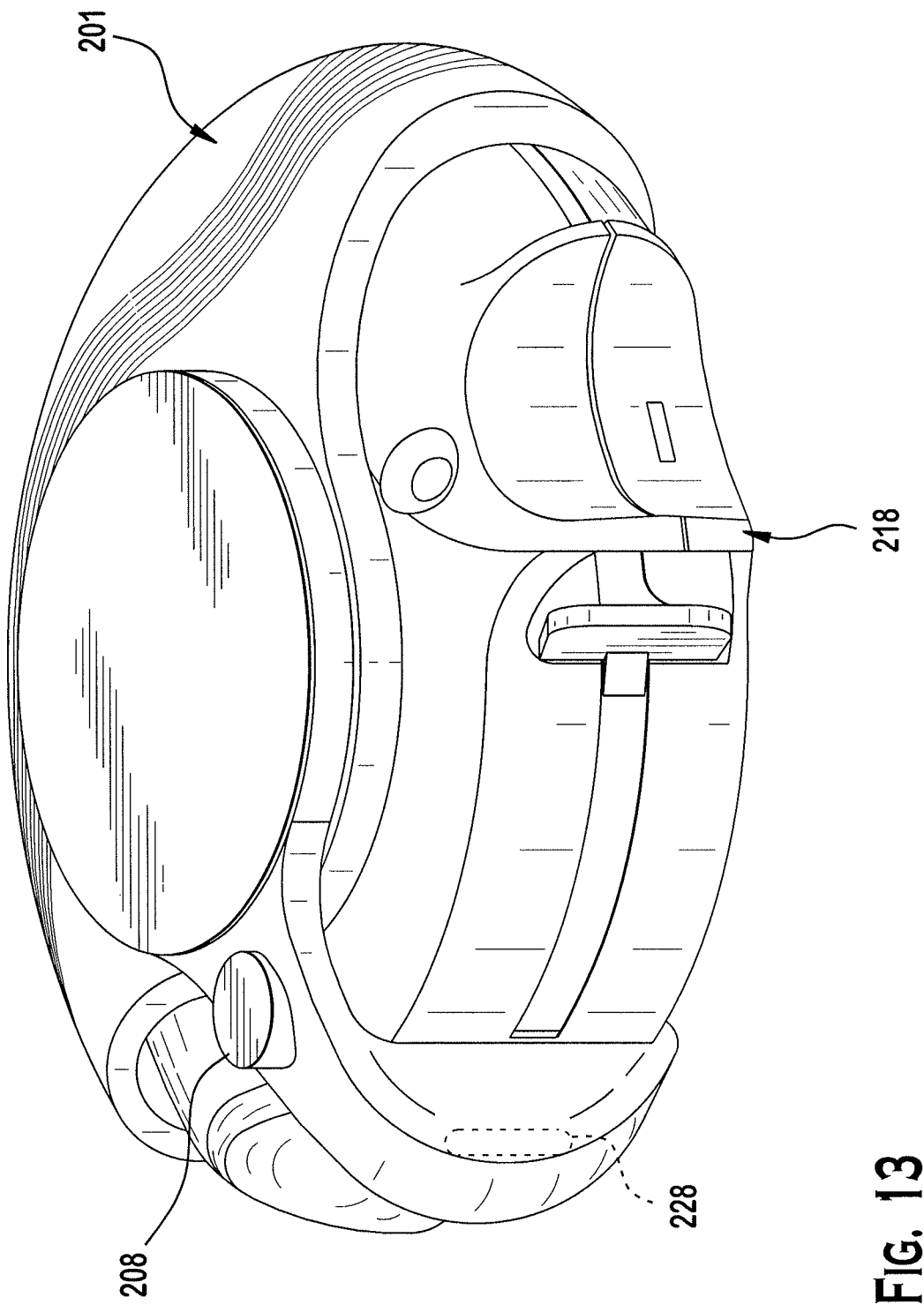
FIG. 13 is a perspective view of an inhaler management system according to an embodiment.

FIGS. 2-9 show an embodiment in the form of a hollow cap 1 for the metered dose inhalers (MDIs) 18. FIGS. 12A-B and 13 show embodiments for attaching to dry powdered inhalers (DPIs). The function of systems attached to DPIs is the same as those attached to MDIs. However, the structure of the attachments will differ based upon the different structures associated with DPIs. For example, FIG. 12A shows a cap 101 attached to a DPI 118 (a turbuhaler DPI) that is actuated by a twisting motion. FIG. 12B shows the DPI 118 without the cap 101. The cap 101 is coupled to a twisting actuator 127 of the DPI 118, and is positioned such that the vents of the cap 101 coincide with an air inlet 128 of the DPI 118. FIG. 13 shows a cap 201 attached to a DPI 218 (a diskus DPI) that is actuated by sliding action. A pressure sensor 208 in the cap 201 is positioned adjacent to an air outlet 228 of the DPI 218, and the structure of the cap 201 surrounding the air outlet 228 introduces resistance to air flow, therefore creating pressure difference, which can be measured as described herein.

Figure 3:
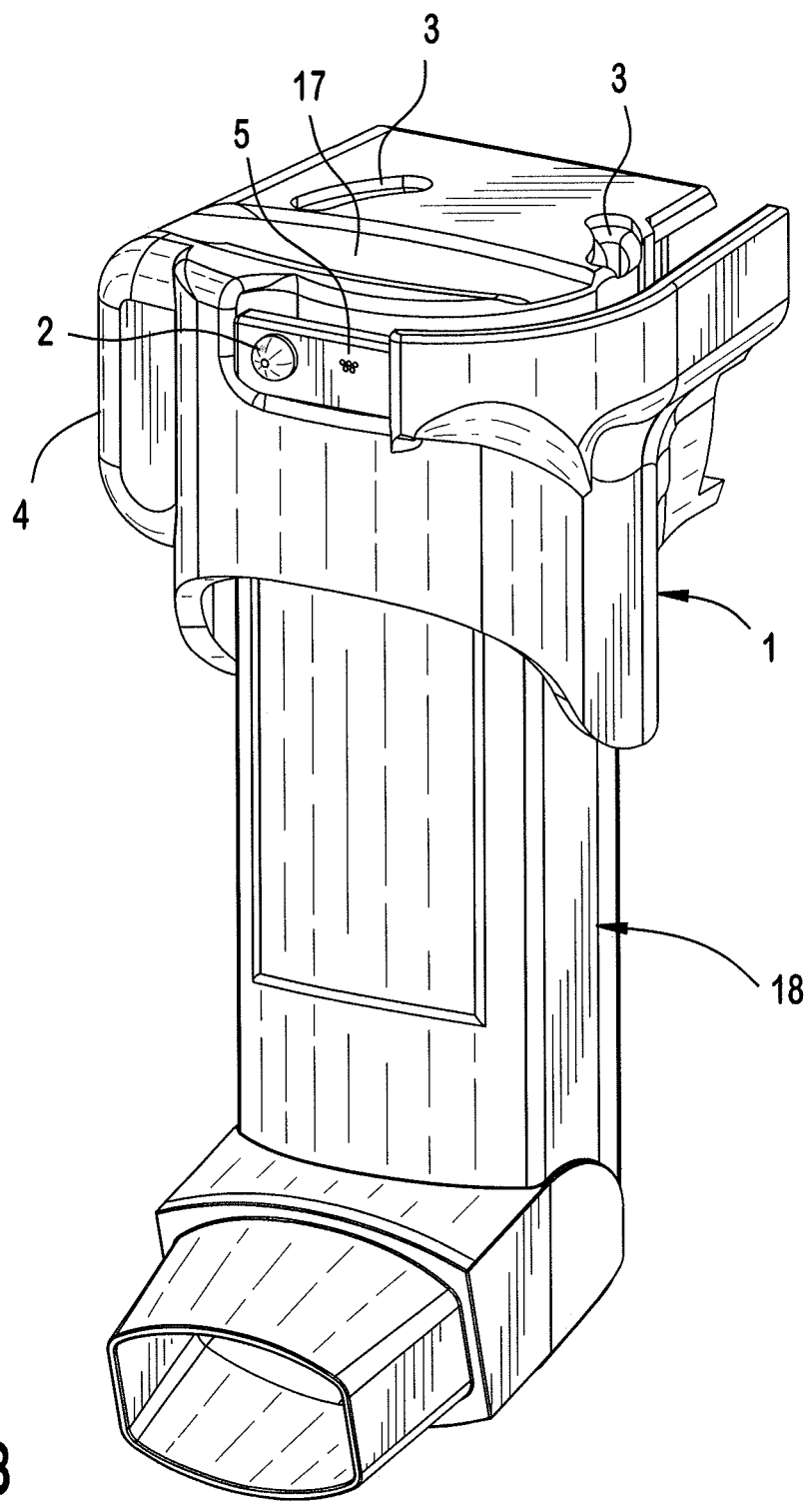
FIG. 3 is a side perspective view of the inhaler management system of FIG. 2.
Figure 4:
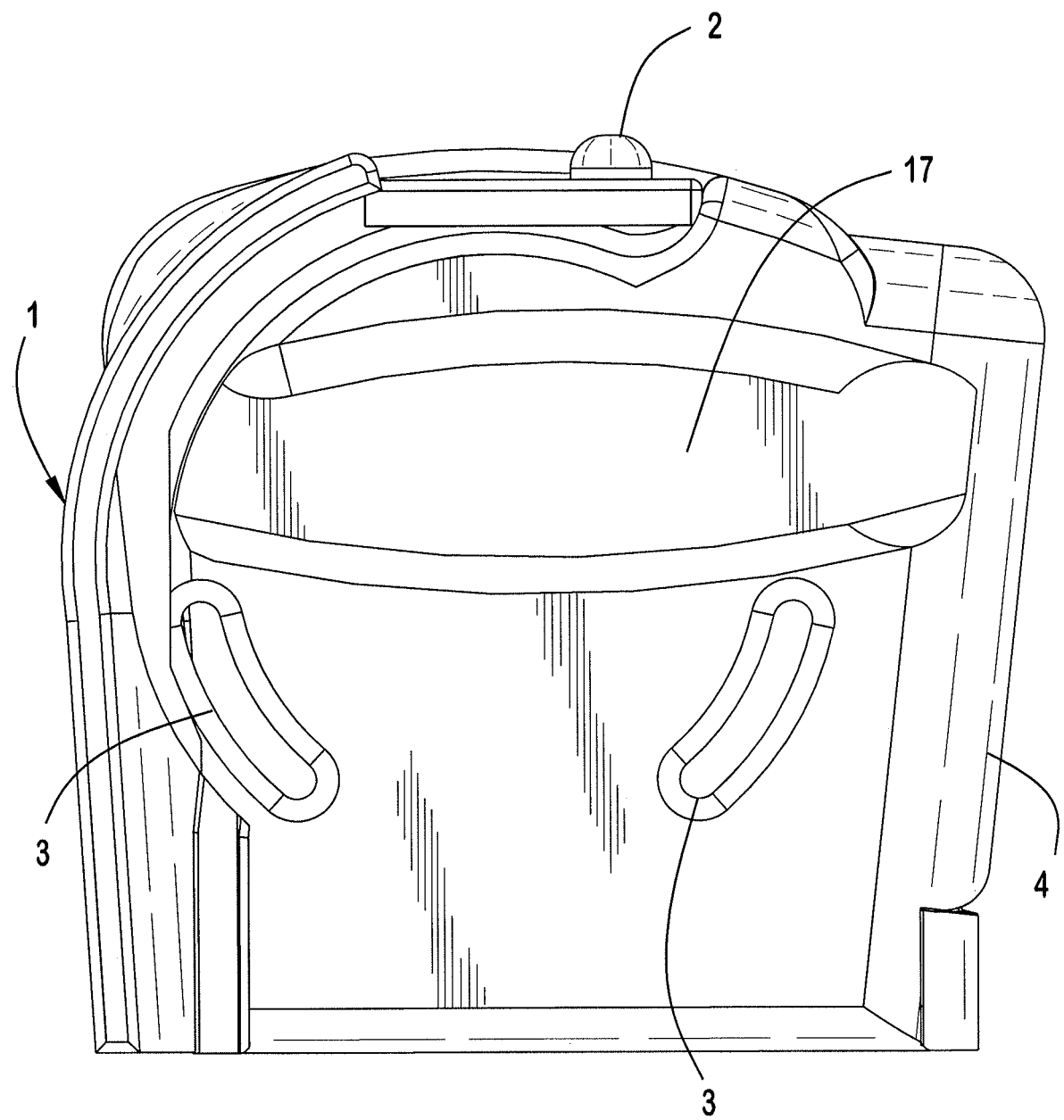
FIG. 4 is a top view of the inhaler management system of FIG. 2.

The cap 1 functions as a small form factor flow meter, designed to fit most commercially available MDIs; the cap size and fit can be also be custom made for a specific MDI and universality of the cap is not a requirement. The cap 1 is shaped according to that of the outer body of MDIs such that the hollow part fits the inhaler 18 snuggly, as shown in FIG. 3. The top of the cap as seen in FIGS. 3, 4, 6 and 7 shows the vent system 3 that allows airflow through the MDI during inhalation and exhalation. The height and shape of the body of the cap 1 is designed to facilitate laminar airflow through the air passage created in the vent 3, cap 1, inhaler 18 and mouth setup. Laminar flow is ensured by a) placing large vents directly on top of the MDI and b) increasing the length of the cap that wraps around the MDI. Size and position of the vent 3 along with the design of the cap 1 is carefully selected in a way that it creates enough pressure differential for the pressure sensor 8 to measure air flow and still keeps the additional resistance to the air flow offered by the cap 1 low. The laminar airflow also allows accurate measurement of the flow rate, especially with the type of pressure sensor 8 used in this design.

Figure 1:
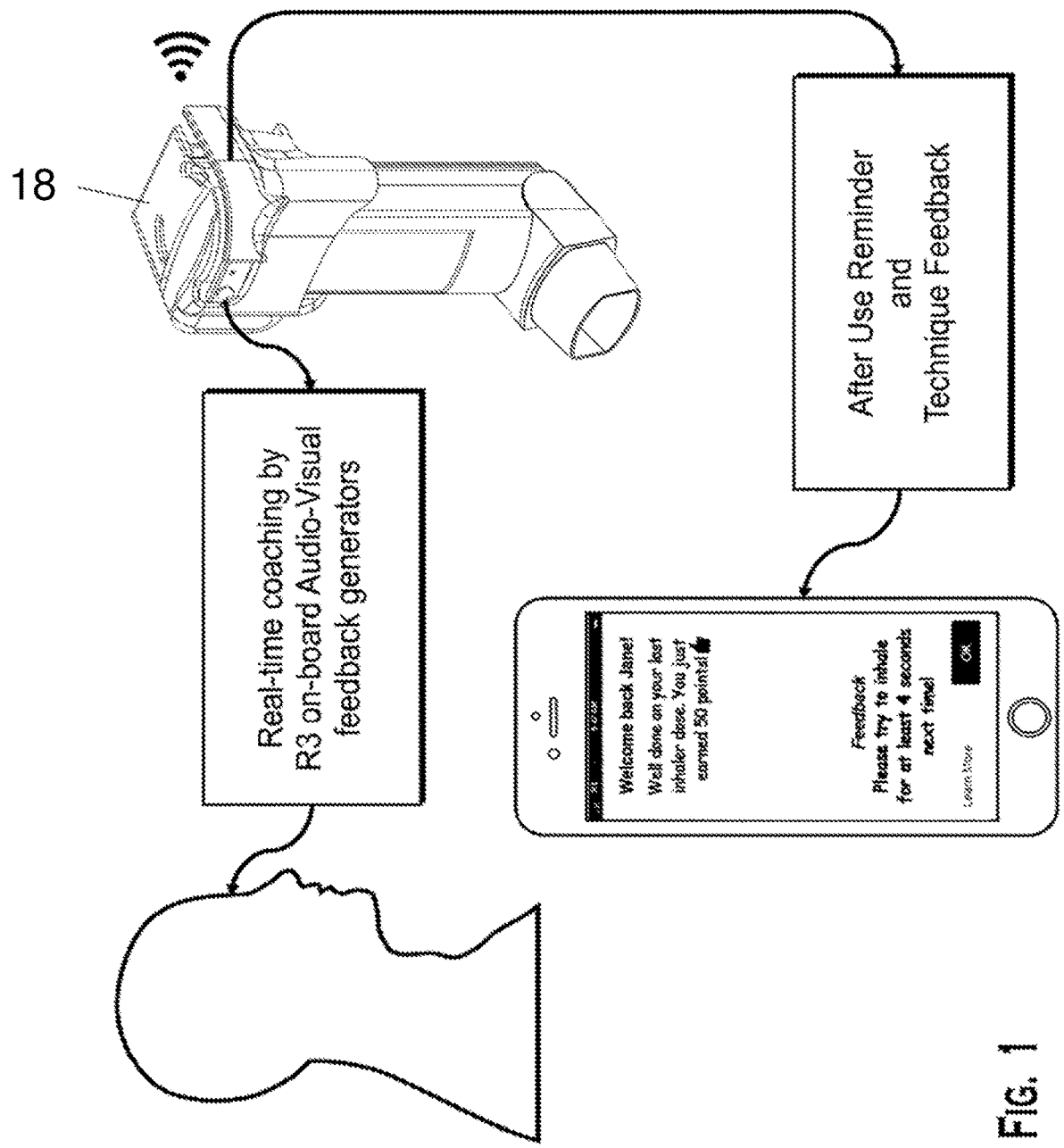
FIG. 1 is an example use of an inhaler attachment according to an embodiment coupled with a smartphone application.
Figure 2:
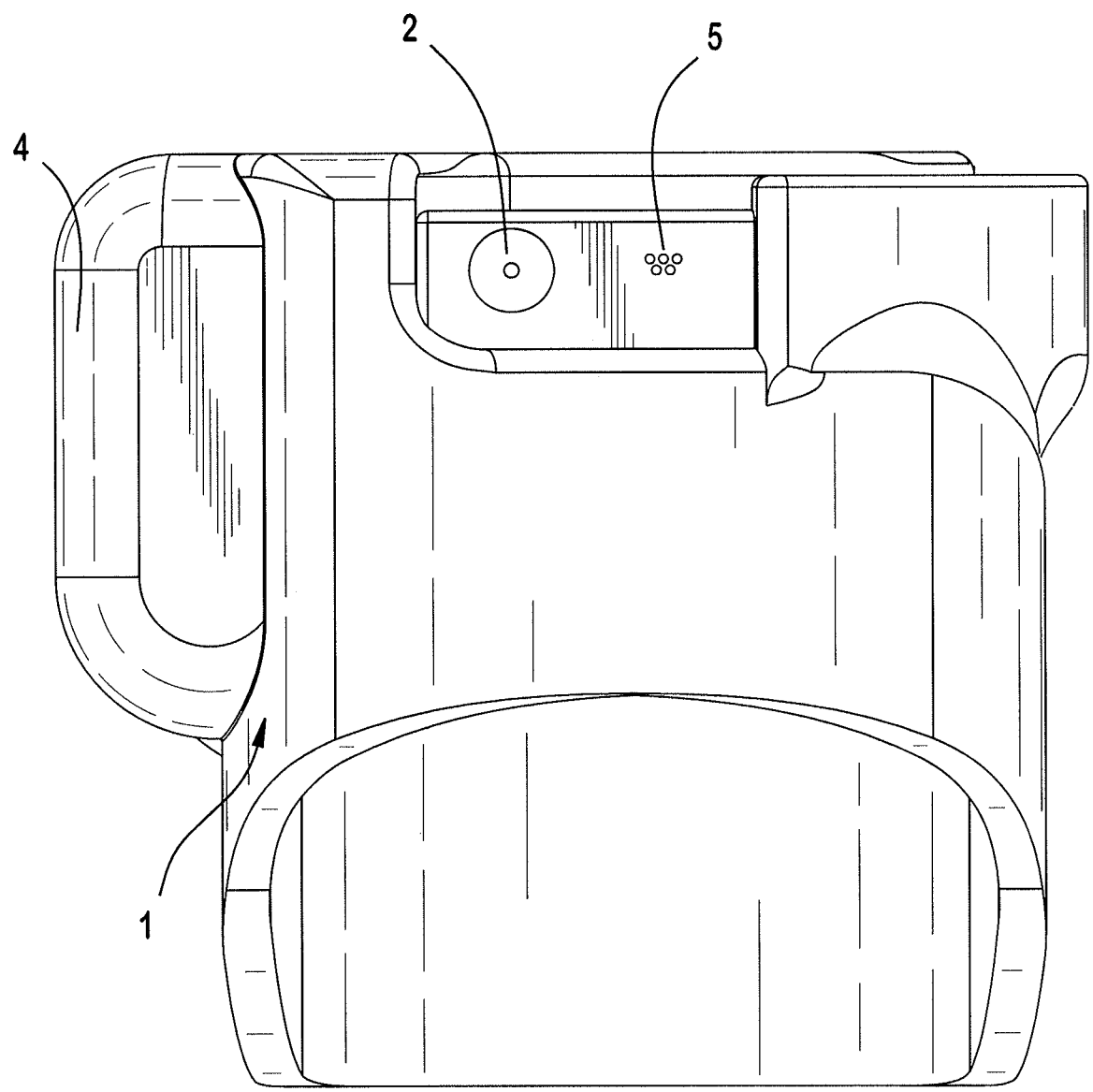
FIG. 2 is a front view of an inhaler management system according to an embodiment.

The electronic cap 1 has an extension 4 that houses the electronics. The front view of the cap 1 as shown in FIG. 2 depicts the real-time feedback system using the multi-color LED 2, buzzer with loudspeaker system 5 and miniature linear motor 16 (shown in FIG. 5) for haptic feedback. Combination of all three systems in different embodiments can be used to give coaching and feedback to a user about correct inhaler use for example, pressing inhaler, breath hold and shaking inhaler before usage.

Figure 5:
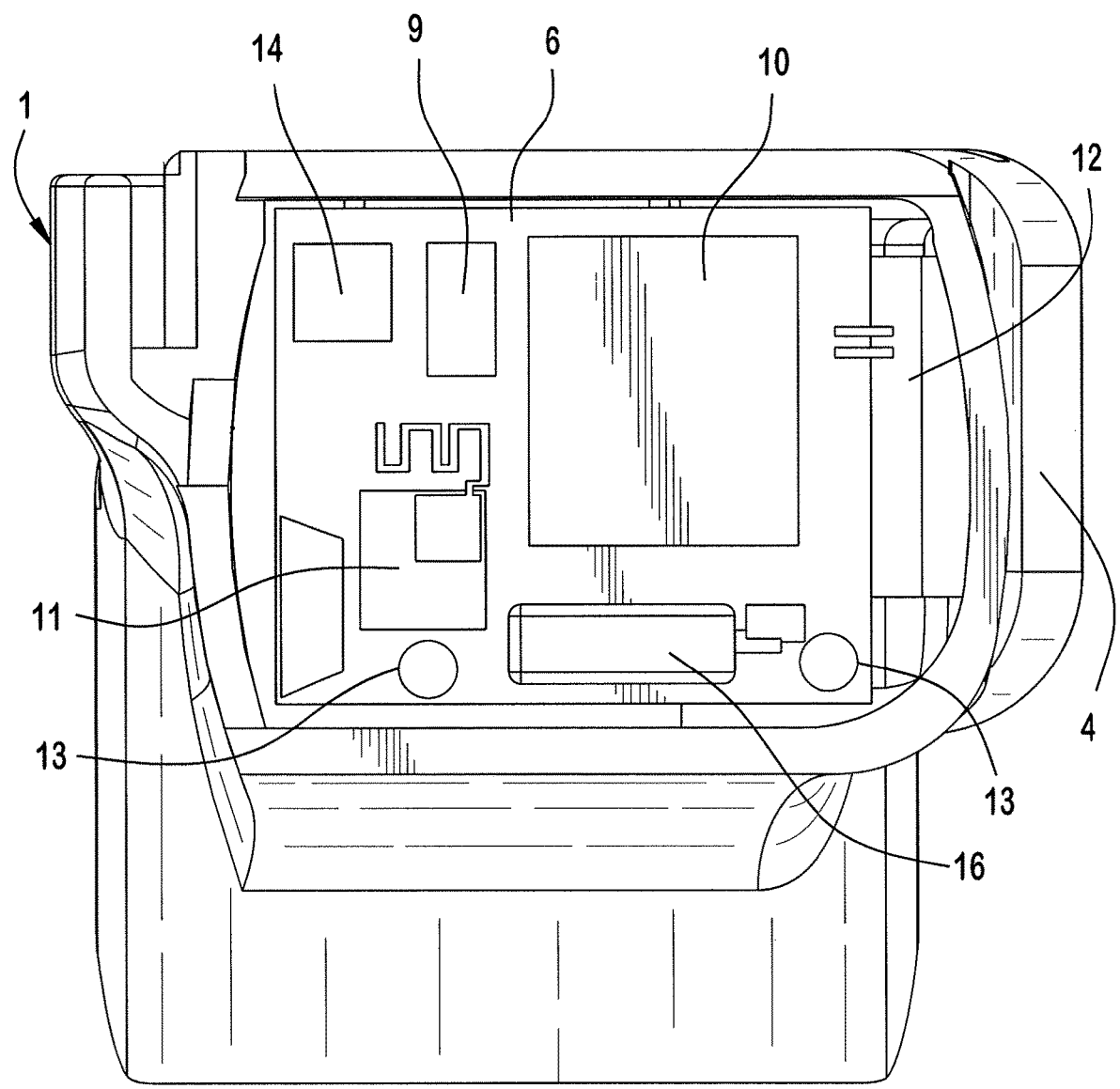
FIG. 5 is a rear view of the inhaler management system of FIG. 2.
Figure 6:
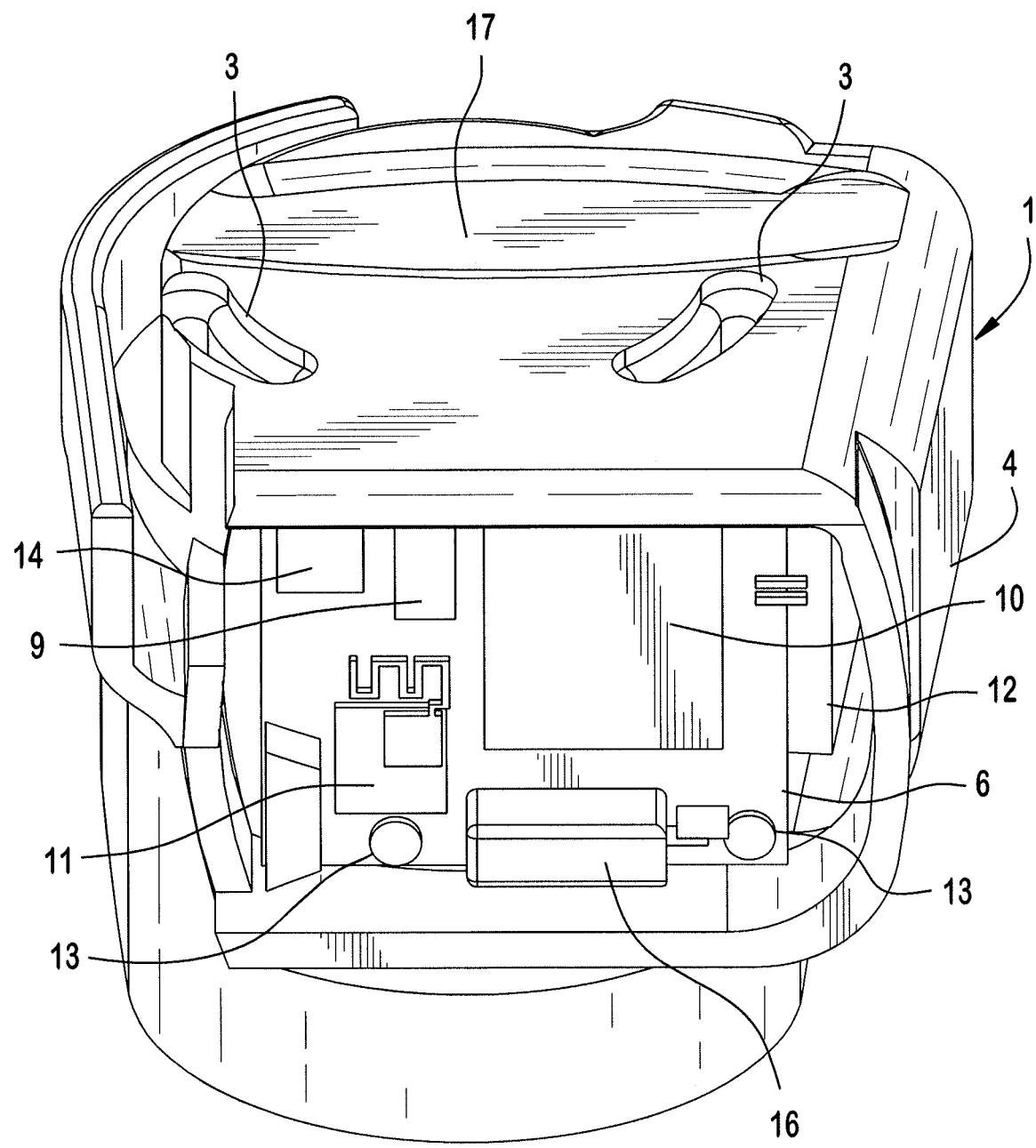
FIG. 6 is a rear perspective view of the inhaler management system of FIG. 2.

FIGS. 5 and 6 show the electronics housed in cap 1 in more detail. The printed circuit board (PCB) 6 includes a force sensor 7, pressure sensor 8, accelerometer 9, micro-controller 10, wireless chipset 11, rechargeable battery pack 12, power management chips (not shown) and other discrete components as needed. The PCB 6 is a flexible/rigid board as shown in FIG. 5 that wraps around the inner wall of the cap 1 connecting the feedback and sensor electronics to the main board in the extension 4.

Figure 7:
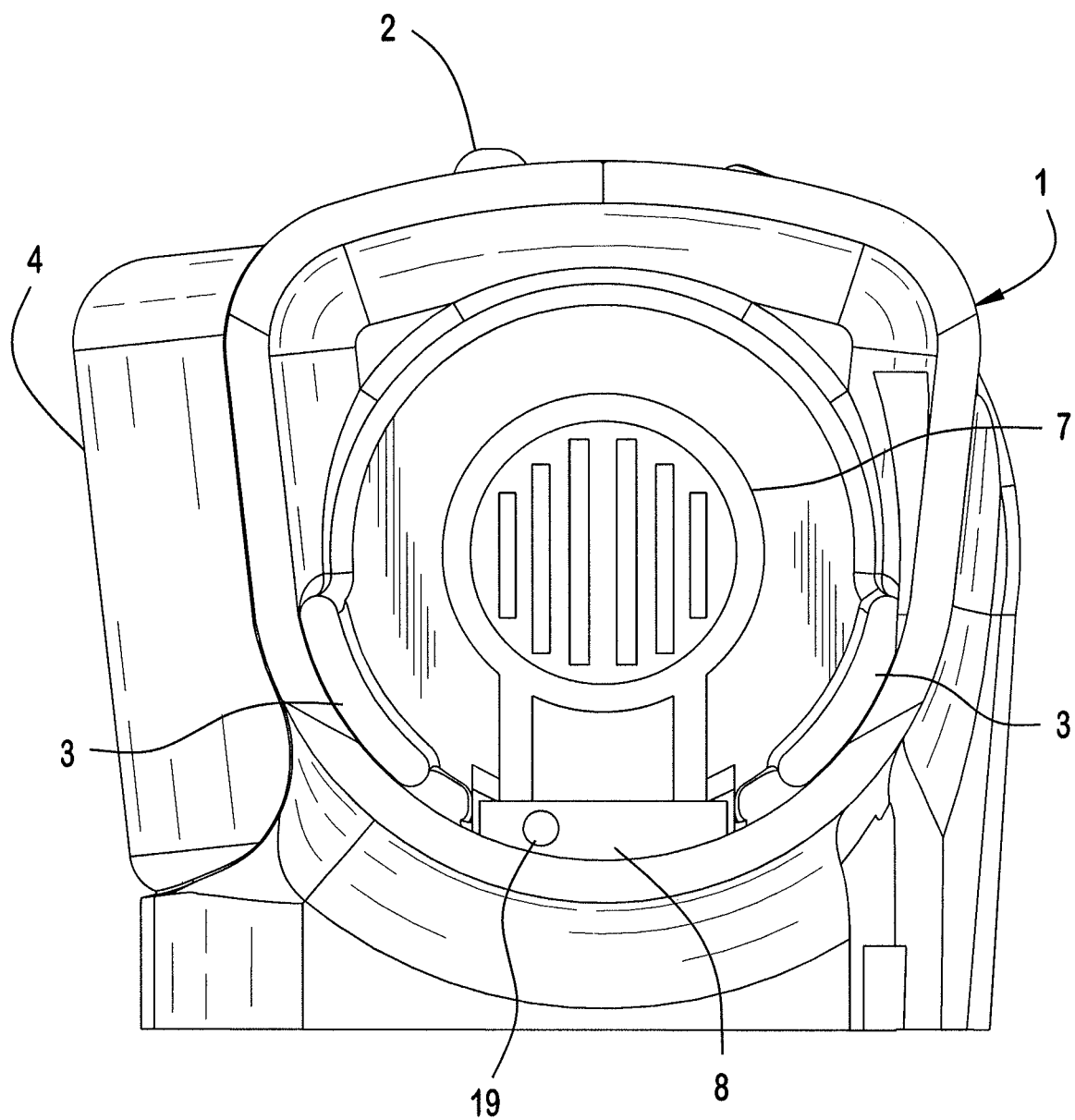
FIG. 7 is a bottom view of the inhaler management system of FIG. 2.
Figure 8:
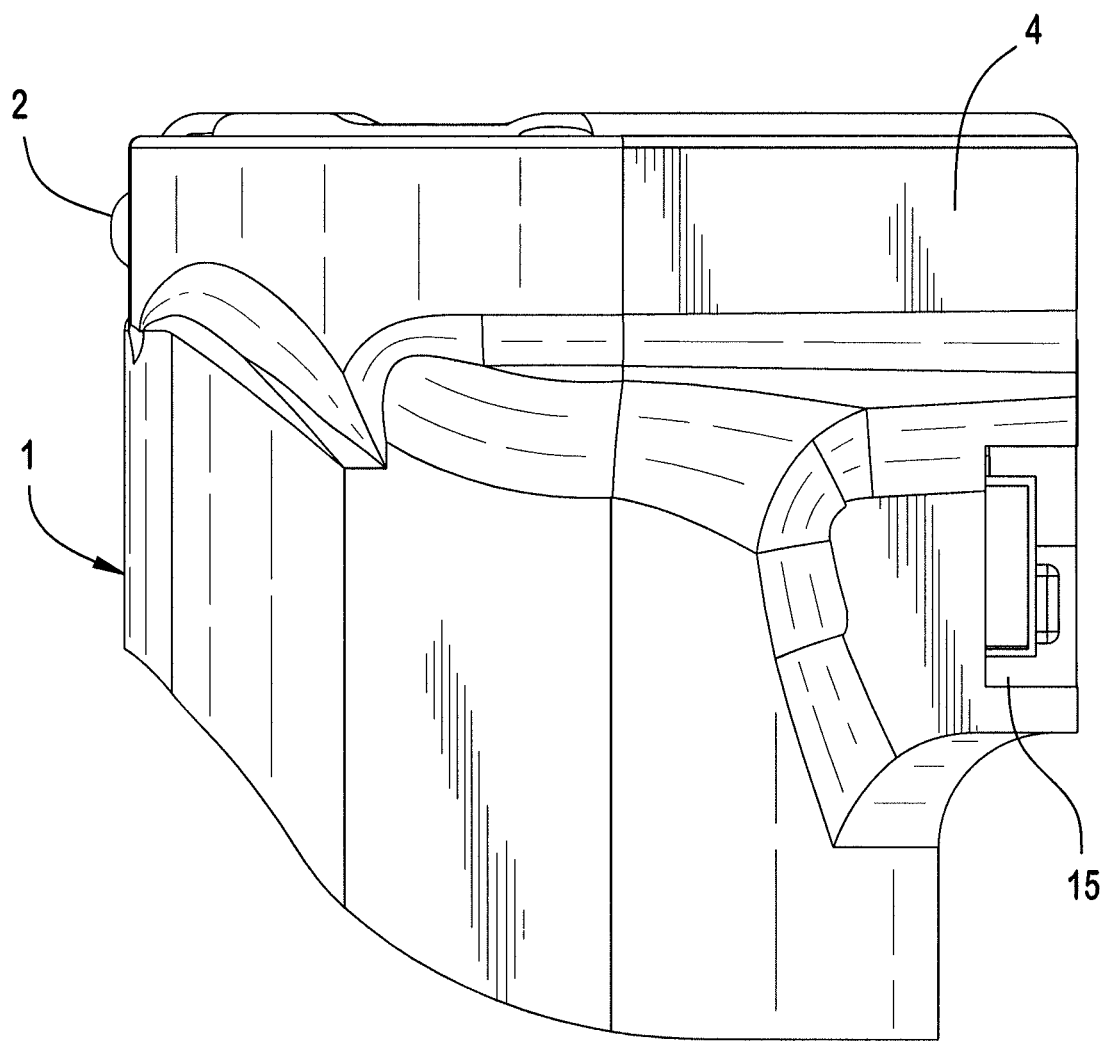
FIG. 8 is a side view of the inhaler management system of FIG. 2.
Figure 9:
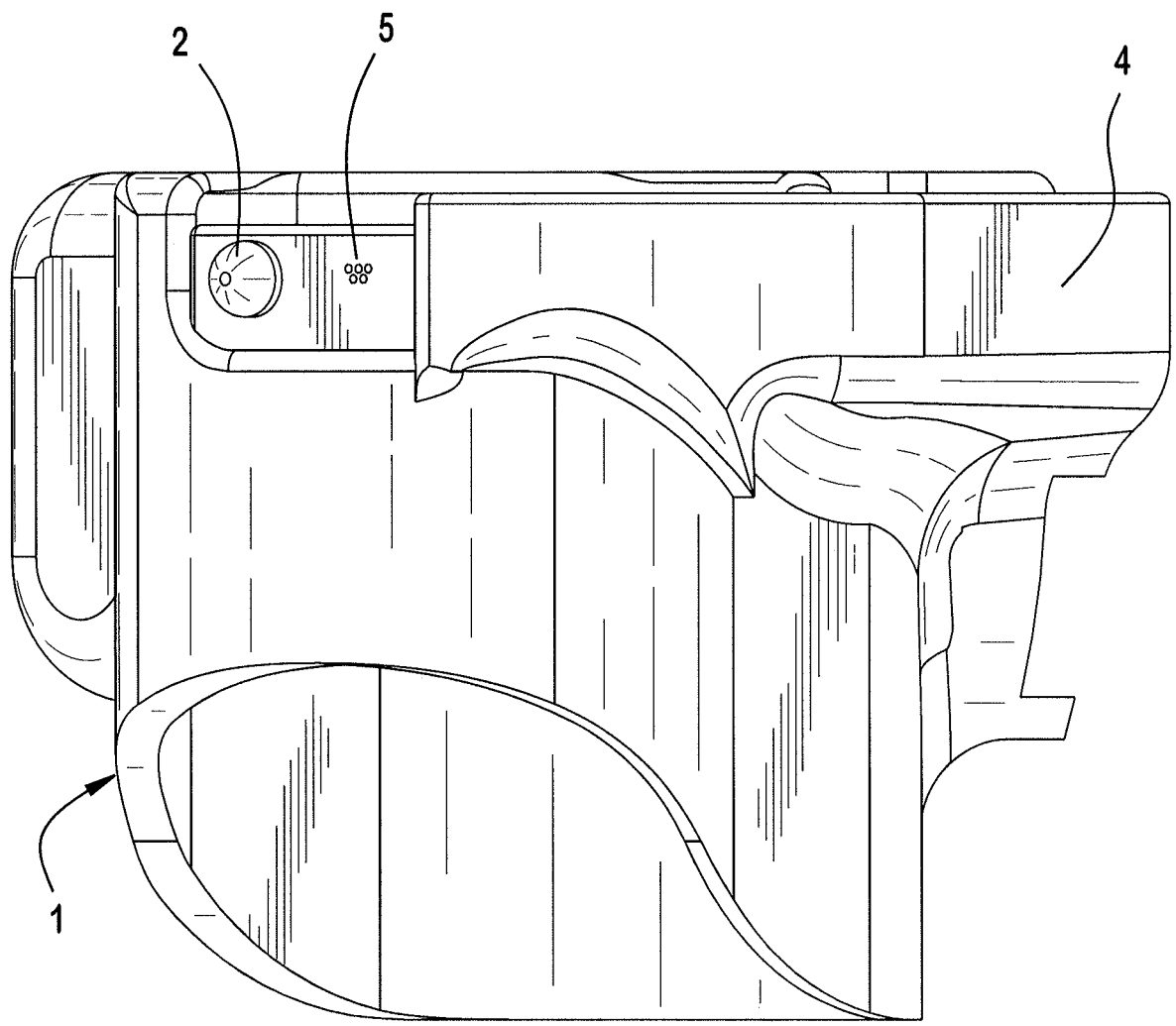
FIG. 9 is a side perspective view of the inhaler management system of FIG. 2.

The primary purpose of the force sensor 7 is to detect whether the inhaler 18 is pressed or not. The force sensor 7 is a transducer that converts the force or pressure applied on the surface of the sensor to a change in its internal resistance. Therefore, the force sensor 7 essentially acts as a variable resistance. The force sensor 7 is placed inside at the roof of the cap 1 as shown in FIG. 7 and is connected to the analog to digital converter (ADC) pins of the microcontroller 10. The change in resistance is converted into the appropriate voltage value by the ADC of the microcontroller 10 and analyzed further to detect the MDI 18 actuation. The force sensor 7 used for this purpose is a flexible paper-thin force sensing resistor such as FSR 402.

The pressure sensor 8 used in the inhaler attachment, as shown in an embodiment in FIG. 7, measures the air flow rate through the cap 1 to analyze the inspiration and expiration rate during the inhaler 18 usage. The cap 1 introduces resistance in the path of respiratory flow in/out of the MDI 18. When air flows through this restriction, it accelerates slightly to conserve the mass flow and as a consequence the air pressure drops. This creates a differential pressure between the space just underneath the cap 1 (internal pressure) and outside the cap 1 (ambient pressure) according to the Bernoulli's principle. The pressure differential changes in proportion to the air flow and can be used to quantify the flow, according to the following expression: $\Delta p \propto Q^2$, where $\Delta p$ is pressure differential and $Q$ is mass flow-rate. The pressure sensor 8 is placed just below the vents 3 at the beginning of the cap extension 4 such that the pressure sensor 8 measures the air pressure present at that point. A pressure sensor port 19 of the pressure sensor 8 is situated on the opposite side (i.e., on the outside of the cap 1) measuring the ambient pressure. Every time the device is turned on, micro-controller 10 zero calibrates the flow-sensor 8 by taking a pressure differential reading between the ambient pressure at the pressure sensor port 19 and the internal pressure just underneath the cap 1 and assigning it with zero flow. Any deviation from this zero flow pressure differential is considered to be positive/negative flow. Accelerometer 9 reading can also be used in conjunction to make sure no motion is present during the calibration to ensure the accuracy. Many commercial transducers measure airflow and convert the resulting measurement into voltage value. The pressure sensor 8 is mounted on to the PCB 6 and connected to the ADC pins of the microcontroller 10 to transfer the air flow rate data for further analysis and feedback generation.

The air flow or pressure sensor 8 is designed to fit inside the electronic cap 1 next to air vents 3. Position of the pressure sensor 8 and vent 3 design of the cap 1 ensures that enough pressure differential is generated between the pressure sensor 8 outside the inhaler 18 in order to accurately measure air flowing through the inhaler body. When the patient inhales through the inhaler 18, the designed inhaler cap attachment 1 has an air passage that lets air enter through the vent 3 into the inhaler 18 body and into the mouth through the mouthpiece. Sensitivity of the pressure sensor 8 and vent 3 size are adjusted such that inhaler cap 1 does not offer significant additional resistance to the air flow ensuring that the inhalation through the MDI 18 is not hindered. Larger vent results into a lower pressure drop requiring sensitive pressure sensor for the measurement. Thus air flow or pressure sensors 8 quantify the air flow rate and volume through the inhaler 18 body, which is representative of the inspiration and expiration by the patients during inhaler 18 usage. In other embodiments, not shown in the figures, any suitable air flow rate sensor, possibly miniaturized, can be used for the same purpose of recording and analyzing inspiration and expiration air flow rates. Also, in other embodiments, alternate electronic components and wireless connectivity methods can be used to achieve the same goals as described by the above embodiment.

The challenge of measuring and improving adherence to inhaler medication can also be addressed by the inhaler attachment. The attachment has built-in timers which can not only timestamp the inhaler usage, but the above-mentioned flow sensors can also confirm whether the medication was dumped outside or actually inhaled by a patient, based on the airflow pattern for typical inspiration through the MDI. Flow sensor reading can be combined with temperature and humidity sensors for increased accuracy. The device can measure some combination of parameters like the flow rate, temperature and humidity of the air inhaled through the mouthpiece of the MDI, and validate that the dosage is taken by a human and also detect the correctness of the inhaler usage technique. Note that the inspiration profile by a human is unique and difficult to reproduce by any other common means, making it difficult for patients to mimic the same maneuver without actually using the inhaler.

The accelerometer chipset (accelerometer combined with a gyroscope) 9 is shown in an embodiment in FIGS. 5 and 6, and is connected to the PCB 6. The accelerometer measures movement and rotation in x, y, z directions. The accelerometer 9 is connected to the microcontroller 10 and detects the number of times and directions in which the cap 1, and in turn, MDI 18 is shaken right before the inhaler dosage. The accelerometer 9 also detects the orientation of the cap 1 (and MDI 18) during the actuation of medication. FIG. 15 shows a chart of exemplary measurements in each of the X, Y, and Z axes taken by accelerometer 9. According to the example shown in FIG. 15, accelerometer 9 detected that the inhaler 18 was shaken six times at approximately time (t)=8 seconds, and the inhaler 18 was shaken six times in an incorrect orientation at approximately t=12 seconds. FIG. 15 also shows that the accelerometer 9 detected an orientation in which the inhaler 18 was not upright from approximately t=12 seconds to t=21 seconds, and thereafter an orientation where the inhaler 18 was upright before approximately t=12 seconds and after t=21 seconds. In this example, whether the inhaler 18 is upright is determined based on the readings of the Z axis relative to the Y axis. In other embodiments, the shaking of MDI 18 may also be detected using air flow and air pressure sensors 8. In this regard, shaking of the inhaler 18 results in increased air flow on the outside of the cap 1, thereby creating a pressure differential between the interior and exterior of the cap 1. Analysis of the measured flow rate based on the pressure readings from sensor 8 can provide an indication that the inhaler 18 was shaken, as shown for example in FIG. 14A at approximately t=1.6 seconds. The microcontroller 10 guides the user on the recommended way to use the inhaler 18 through the data obtained from the sensors and the feedback system including the LED indicator 2, loud speakers 5 and haptic motor 16. The feedback mechanism alerts the user on incorrect MDI 18 usage in real-time such that the patient can immediately fix the orientation and continue with the dosage procedure.

As shown in FIGS. 14A-C and 15, the measured flow-rate, accelerometer data and force sensor data are signals as a function of time. Thus, the information collected from all the sensors regarding number of shakes, orientation, MDI actuation, and breathing flow rate are synchronized in time. This allows quantifying the correctness of 'coordination' during MDI usage, where coordination refers to the balance in time between start of inhalation and MDI actuation. The combined data can also detect and store other stages of incorrect MDI usage.

The capacitive touch film 17 is embedded on the grooves for the finger at the top of the cap 1. The capacitive touch film 17 is protected by a thin sheet of plastic, acrylic or other thin material as part of the cap's 1 outer case. Capacitive film 17 will be monitored by either dedicated capacitive touch sensor chipset or micro-controller 10. In one embodiment, the ultra-low power capacitive touch sensor is always ON looking for an external human touch, unlike other components on the board 6. Upon sensing the human touch, controller 10 chipset turns the board 6 on and then the microcontroller 10 software differentiates between accidental touch or intentional inhaler 18 use by determining the duration of human touch, force sensor 7 value, orientation information from accelerometer 9 and flow values from pressure sensor 8 and comparing those detected values with predetermined values stored in on-board memory 14 that are indicative of an accidental touch. According to the example shown in FIG. 14B, an intentional inhaler 18 use is detected at approximately t=5 seconds. If the device software decides it was an accidental touch, the controller 10 turns the board 6 off immediately to save power. Controller 10 also turns the board 6 off after prolonged duration of inactive status. For example, the controller 10 turns the board 6 off after 10 seconds of no human touch and no motion.

The main component of the electronics powering the functionalities of cap 1 is the low power microcontroller 10 as shown in FIGS. 5 and 6. The microcontroller 10 communicates with all the peripherals including force sensor 7, pressure sensor 8, accelerometer 9, feedback system 2 and 5, wireless chip 11, etc. Since the microcontroller 10 draws much less power from the battery 12, the device requires less frequent recharges. The device can be recharged with a USB charging cable, with the connector 15 shown in FIG. 8. The microcontroller 10 communicates with the sensors to obtain information about the state of MDI 18 usage, record the sensor information and provide appropriate feedback to the user. The microcontroller 10 has internal analog to digital converters for converting the sensor information into digital form for storage and interpretation. Once the information pertaining to one MDI 18 usage is recorded completely, the data is stored in the onboard flash storage 14. When the gadget comes in the vicinity of the paired mobile device, the microcontroller 10 sends all the stored information through wireless interface such as Bluetooth™ to the mobile device.

FIGS. 5 and 6 also show the low power wireless chipset 11. The main function of the wireless chip 11 is to transfer data from the device to the personal mobile device for viewing, analysis and sharing with caregivers. The wireless interface can be Bluetooth™ 4.0 LE, WiFi™ or other low power standardized or custom methods for wireless connectivity. When supported, the personal mobile device will require one time pairing with the device 1 and then will automatically connect whenever the mobile device is in the vicinity of the device 1.

Another feature of the low power MDI usage monitoring device 1 is an onboard storage 14 for all the data collected. The device 1 can store inhaler usage information from all the sensors in real-time on an on-board low power permanent serial flash storage 14. This information may or may not be retained by the device 1 after uploading it to a secure online storage. The complete information from all the sensors quantifying the MDI usage technique is stored on the on-board memory 14 in the inhaler attachment (electronic cap 1) for each inhaler 18 usage and transferred to a remote facility or a local storage using any number of possible communication techniques.

Figure 10:
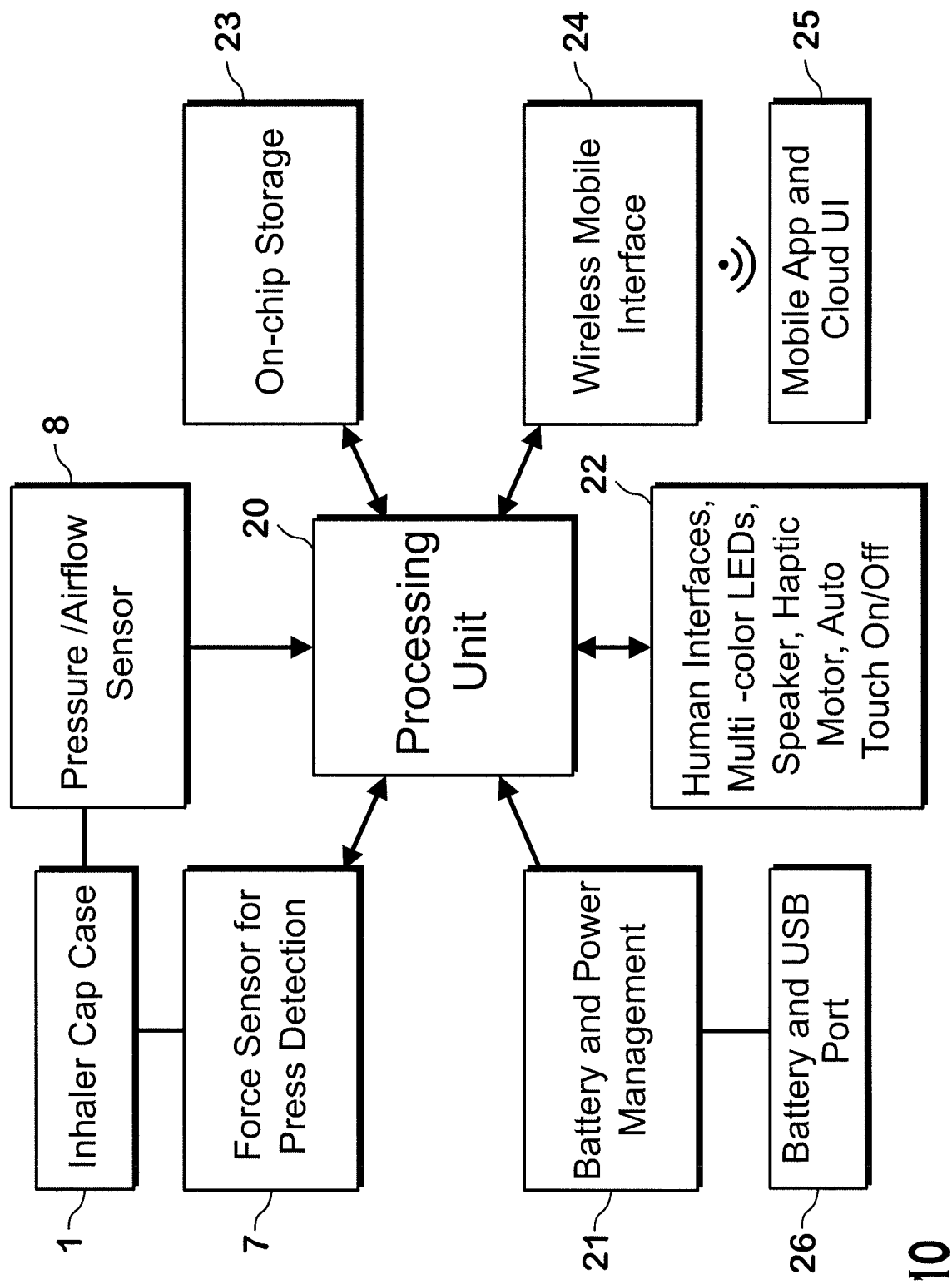
FIG. 10 is a block diagram of the inhaler management system of FIG. 2.

FIG. 10 shows a block diagram to represent an embodiment of the inhaler management system, previously described with respect to FIGS. 2-9. The block diagram shows a processing unit 20 that is housed in the invented electronic device and is connected to all the sensors on the device. As an example, the sensors shown in the block diagram are force sensor 7 and pressure sensor 8, situated in the physical proximity of the MDI. The processing unit 20 communicates with the sensors, battery management system 21 (including, for example, a battery and USB port 26), human interface system 22, data storage 23 and wireless communication system 24. The arrows show that data is transferred between the various systems on the device and the processing unit 20. The Bluetooth™ mobile interface is an example wireless communication method implemented in one of the embodiments. The wireless communication transfers the data from the sensors or storage systems to the mobile app and cloud computing system 25 through the processing unit 20.

Figure 11A:
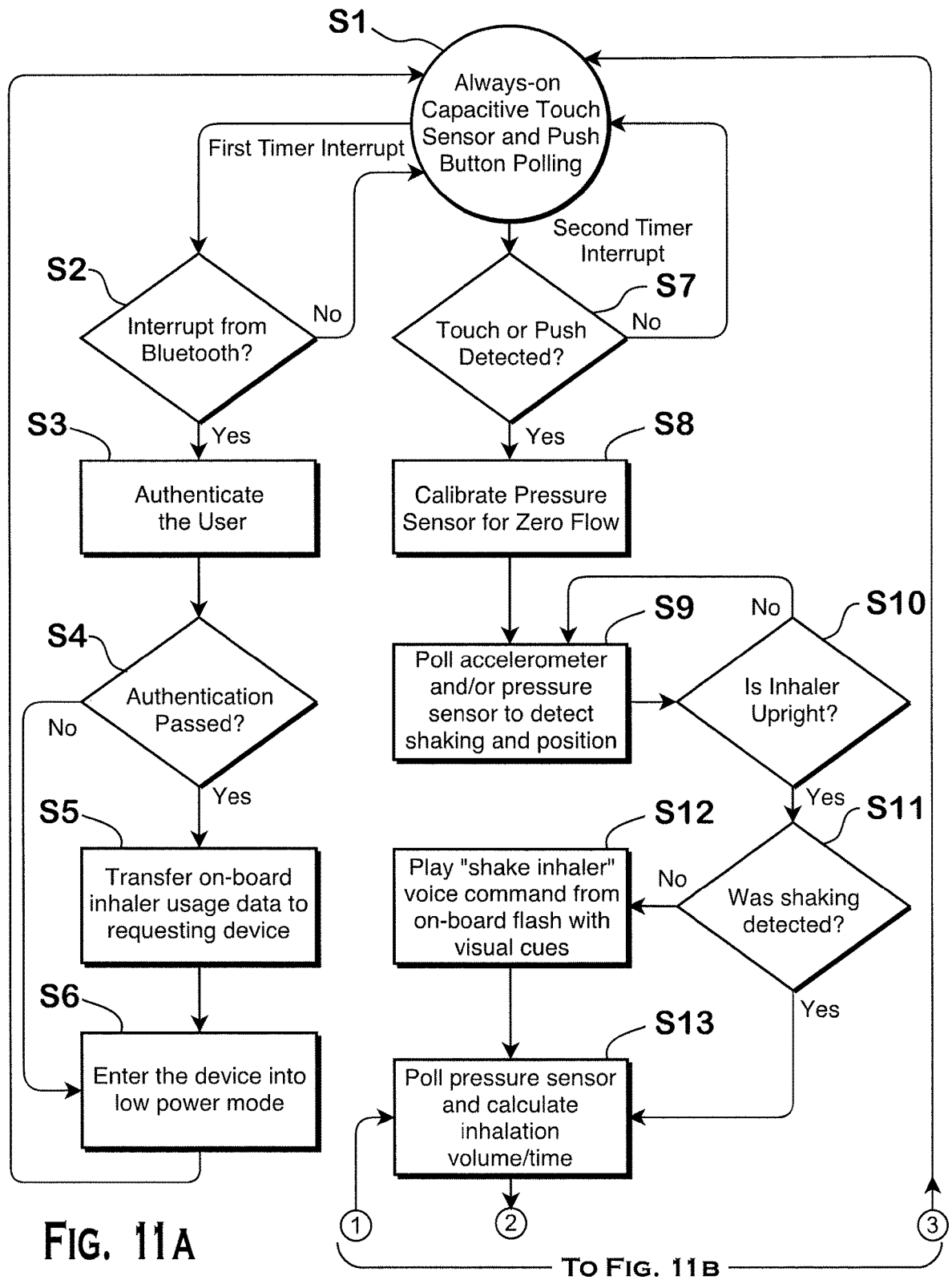
FIGS. 11A and 11B are a flow chart of an exemplary coaching program algorithm.
Figure 11B:
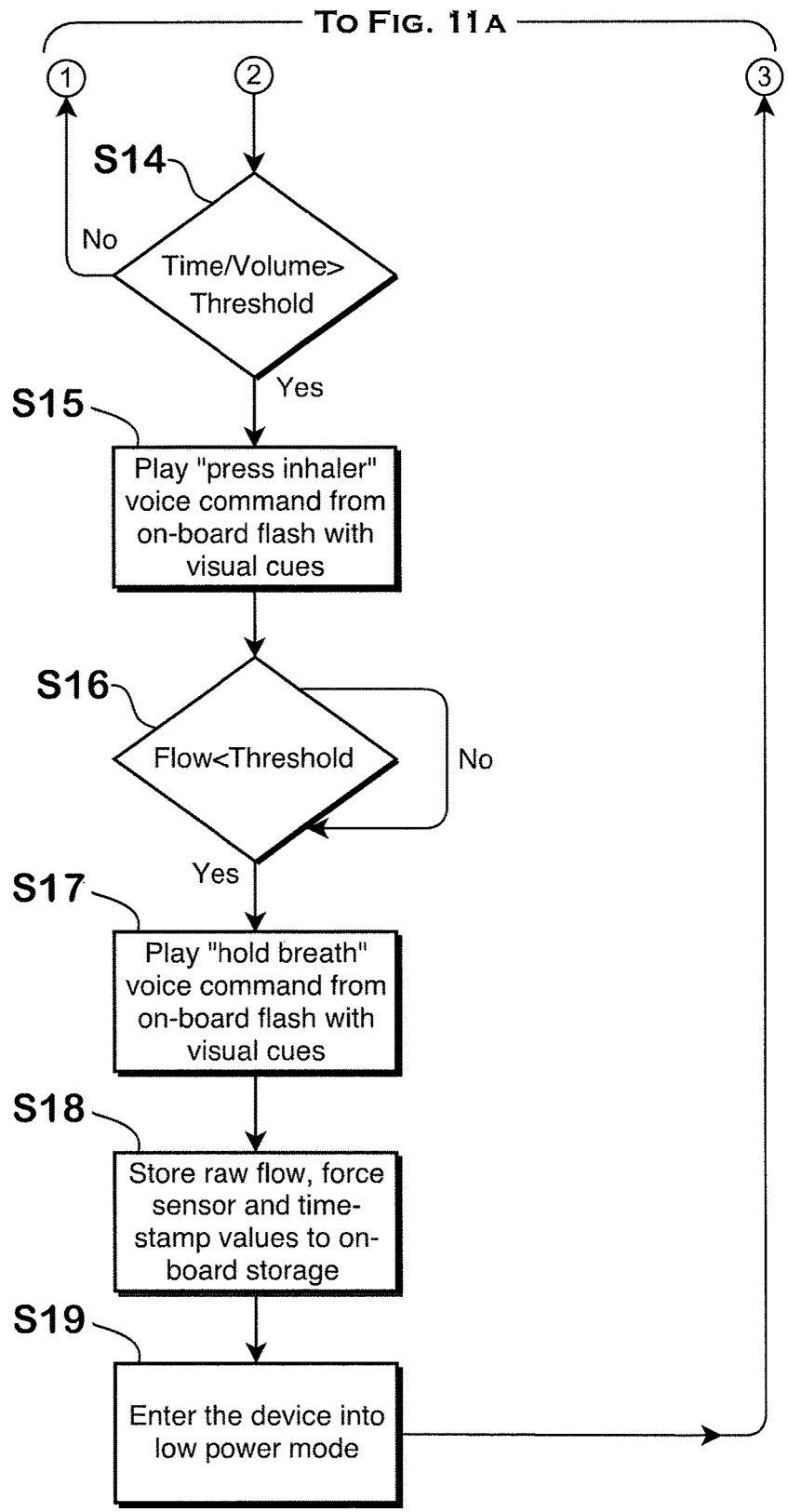

Further, one of the example embodiments provides real-time training and guidance to users for operating the MDI. The device detects the MDI usage by the user to provide real-time assistance in the inhaler usage and also record the usage technique. FIGS. 11A and 11B show an exemplary flow chart to explain the working procedure of such a feedback system and detail the functioning algorithm behind such an embodiment.

With reference to the exemplary flow chart of FIGS. 11A and 11B, in step S1, the system begins according to one of several predetermined processes depending upon whether the system is always on, based on detection of capacitive touch, or push button polling. If an interrupt from Bluetooth™ (First Timer Interrupt, FIG. 11A) is detected at step S2, the process proceeds to step S3 where the Bluetooth™ user is authenticated. If the user authentication does not pass, NO at step S4, the process proceeds to step S6, where the device is placed in a low power mode. If user authentication is passed, YES at step S4, the process continues to step S5 where on-board inhaler usage data is transferred to the requesting Bluetooth™ device. The device is then placed in a low power mode in step S6.

With respect to the detection of capacitive touch or push button (Second Timer Interrupt, FIG. 11A), the process proceeds from step S1 to step S7. If no touch or push is detected, NO at step S7, the process returns to step S1. If a touch or push is detected, YES at step S7, the process proceeds to step S8 in which the pressure sensor 8 is calibrated for zero air flow. Next, at step S9, the system polls accelerometer 9 and/or pressure sensor 8 to detect shaking of the inhaler 18 and position/orientation of the inhaler 18. If the inhaler 18 is not upright, NO at step S10, the process returns to step S9. If the inhaler 18 is upright, YES at step S10, the process continues to step S11, where the detection of shaking of the inhaler 18 is determined. Detection of shaking of the inhaler 18 can be accomplished by the microcontroller 10 by either polling the pressure sensor 8 or by polling the accelerometer 9. If shaking is not detected, NO at step S11, a notification is provided to the user to shake the inhaler 18 at step S12. For example, a "shake inhaler" voice command may be played through feedback speaker 5 or visual cues may be provided through the LED indicator 2. If shaking is detected, YES at step S11, the process continues to step S13 where pressure sensor 8 is polled to calculate inhalation volume/time (duration) through the inhaler device. A timer calculates time spent during inhalation, and it is then used to calculate inhaled volume by integrating flow values over measured time. Next, at step S14, the calculated instantaneous inhalation volume/time is compared to a predetermined threshold. The threshold is the minimum inhalation volume/time to determine whether the user has started inhaling through the inhaler (and may be predetermined based upon data concerning typical inhaler usage). If the inhalation volume/time is greater than the threshold (i.e., inhalation has started), the algorithm proceeds to step S15, where the system provides a notification to the user to dispense medication from the inhaler 18. For example, a "press inhaler" voice command may be played through feedback speaker 5 or visual cues may be provided through the LED indicator 2. At step S16, the calculated air flow is compared to another threshold. This threshold determines if the inhalation by the user has been completed, and may also be predetermined based upon typical inhaler usage. If the air flow is not less than the threshold (the user is still breathing), NO at step S16, then the device continues to record the inhalation and other inhaler usage parameters (force sensor value, air flow, humidity, temperature, etc.). If the air flow is less than the threshold, YES at step S16, the process continues to step S17 where a notification is provided to the user regarding inhaler 18 usage. For example, a "hold breath" voice command may be played through feedback speaker 5 or visual cues may be provided through the LED indicator 2. Next, at step S18, the raw air flow (corresponding to the pressure reading of pressure sensor 8 converted into flow value), force sensor readings, and timestamp values are stored to the on-board storage 14. Finally, at step S19, the device enters a low power mode. Additionally, a timer also calculates time spent at every step. If any process takes longer time than predetermined values, it is flagged as an error and recorded along with other sensor data. The system moves to low-power state after the error event.

Figure 14A:
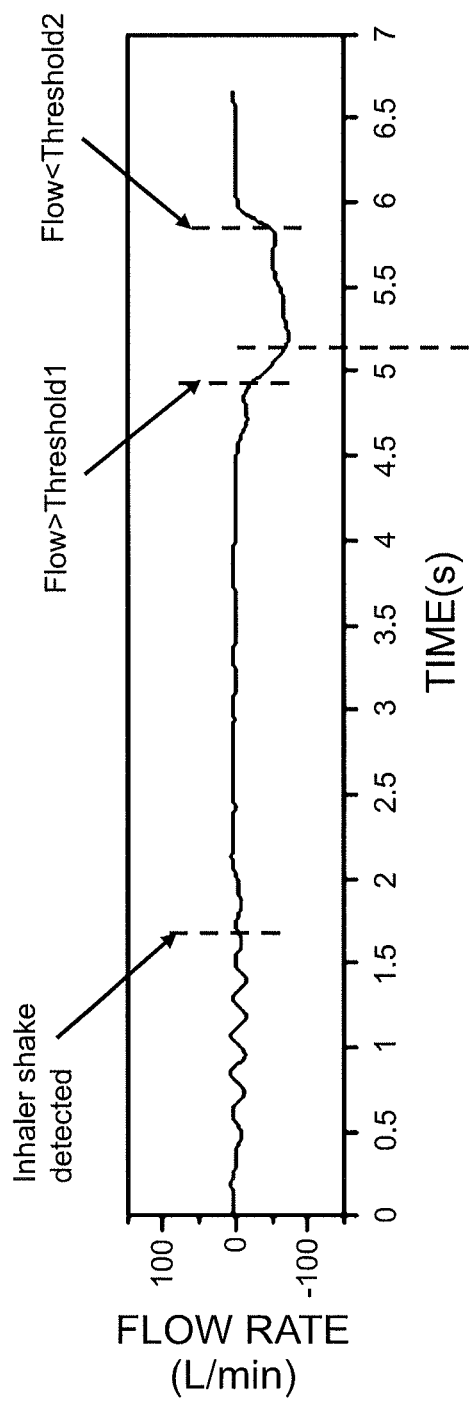
FIG. 14A is a chart showing flow rate according to an embodiment.
Figure 14B:
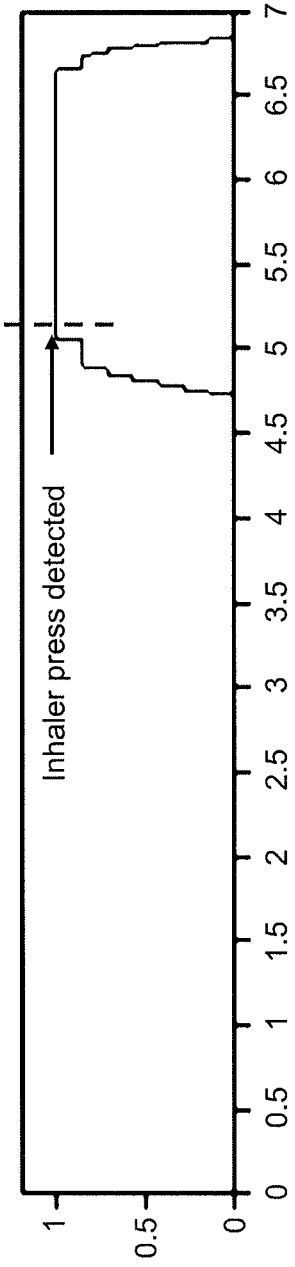
FIG. 14B is a chart showing force according to an embodiment.
Figure 14C:
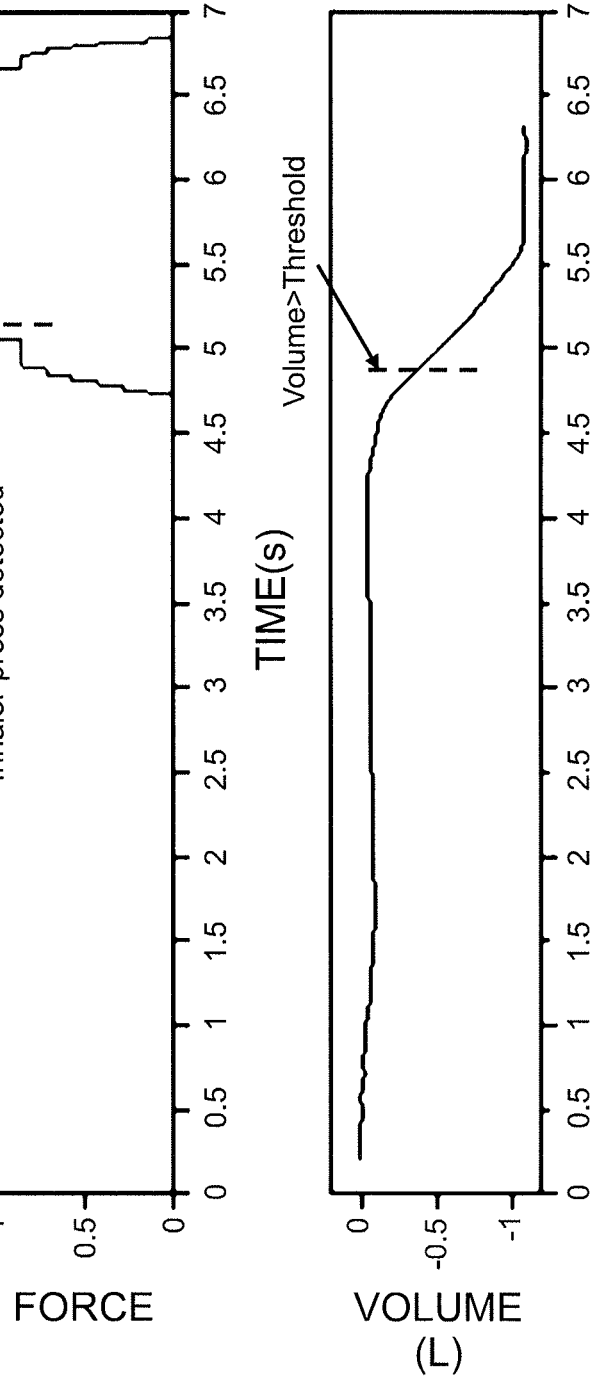
FIG. 14C is a chart showing volume according to an embodiment.
Figure 15:
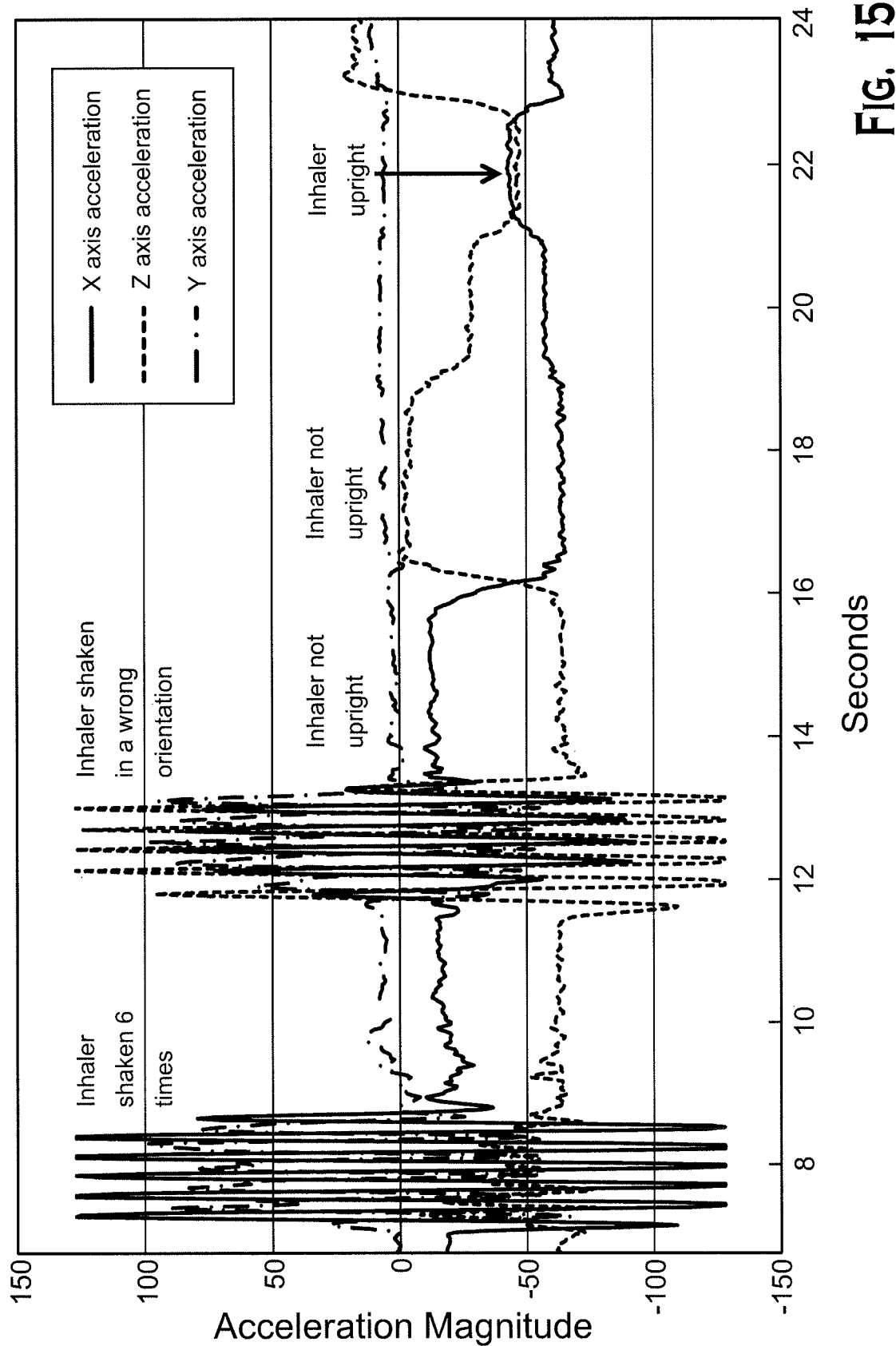
FIG. 15 is a chart showing acceleration magnitude according to an embodiment.

As shown in FIGS. 14A and 14C, exemplary readings of flow rate and volume are provided, respectively. According to FIG. 14A, once the flow rate, as determined from pressure sensor 8 readings, is determined to be greater than a first predetermined threshold (indicated as Threshold1), the system assumes that inhalation has started and a "press inhaler" prompt is generated (at approximately t=4.9 seconds in FIG. 14A). Once the flow rate is determined to be less than a second predetermined threshold (indicated as Threshold2), the system assumes that inhalation has been completed and a "hold breath" prompt is generated (at approximately t=5.8 seconds in FIG. 14A). As shown in FIG. 14C, the determination of whether inhalation has started could also be based upon the measured volume. Once the measured volume is determined to be greater than a third predetermined threshold, the system assumes inhalation has started and a "press inhaler" prompt may be generated.

While the invention has been disclosed with reference to certain preferred embodiments, numerous modifications, alterations, and changes to the described embodiments are possible without departing from the sphere and scope of the invention, as defined in the appended claims and their equivalents thereof. Accordingly, it is intended that the invention not be limited to the described embodiments, but that it have the full scope defined by the language of the following claims.

What is claimed is:

1. A detachable cap for measuring usage of an inhaler, comprising:
   a hollow receiving portion adapted to removably receive the inhaler and configured to snugly fit an outer body of the inhaler, wherein the receiving portion further comprises a rigid roof portion;
   a vent, formed in the roof portion of the detachable cap and located above a plane defined by a top surface of a canister located in the inhaler, to allow a flow of inhaled air through the detachable cap to the inhaler, the vent defined by a fixed size opening through the roof portion, wherein a height of the cap and the size of the vent are configured to facilitate laminar air flow through the cap and vent, and configured to create a constant resistance to the flow of inhaled air during use of the inhaler;
   an electronic circuit including a controller coupled to a storage device and a power source;
   a pressure sensor inside the detachable cap, underneath the roof portion, and adjacent to the vent, wherein the pressure sensor comprises a pressure sensor port situated on the outside of the detachable cap, the pressure sensor communicatively coupled to the controller and adapted to detect a first internal air pressure within the detachable cap, underneath the roof portion, and adjacent to the vent, and the pressure sensor port adapted to detect a first ambient pressure outside the cap, wherein the controller is programmed to calculate an inhaled airflow rate through the detachable cap based on the difference between the first detected ambient pressure and the first detected internal air pressure based on Bernoulli's principle and to store the calculated airflow rate in the storage device.

2. The detachable cap of claim 1, further comprising a force sensor in the roof portion of the detachable cap, the force sensor being communicatively coupled to the controller and adapted to detect a user force applied to the roof portion of the detachable cap, wherein the controller is programmed to calculate the air flow rate through the detachable cap when the force sensor detects the user force applied to the roof portion of the detachable cap.

3. The detachable cap of claim 2, further comprising an accelerometer communicatively coupled to the controller, the accelerometer being adapted to detect an orientation of the inhaler, wherein the controller is programmed to:
determine whether the inhaler has been shaken based on measurements taken by at least one of the accelerometer and the pressure sensor,
store the detected orientation of the inhaler and the determination of whether the inhaler has been shaken in the storage device, and
when the detachable cap is subjected to the user force and the inhaler has not been shaken, the controller is programmed to execute instructions for providing a notification to a user to shake the inhaler.

4. The detachable cap of claim 3, further comprising:
a timer communicatively coupled to the controller, the timer adapted to apply a timestamp corresponding to usage of the inhaler,
wherein the controller is programmed to store actual parameters of inhaler usage including the calculated air flow rate, the user force, the detected orientation of the inhaler, the determination of whether the inhaler has been shaken, and the applied timestamp in the storage device as a function of time,
wherein the storage device includes a predetermined range of parameters that define recommended inhaler usage, and
wherein the controller is programmed to compare the actual parameters of inhaler usage with the predetermined range of parameters to determine whether the inhaler usage is recommended inhaler usage.

5. The detachable cap of claim 4, further comprising:
at least one of a light emitting diode, a haptic motor, and a speaker,
wherein the controller is further programmed to execute instructions for providing a notification to the user related to whether the inhaler usage is recommended inhaler usage, the notification being in the form of audio cues through the speaker, visual cues through the light emitting diode, or haptic cues through the haptic motor.

6. The detachable cap of claim 1, wherein the receiving portion further comprises a rigid side surface.

7. The detachable cap of claim 1, wherein the pressure sensor is further adapted to detect a second internal air pressure within the detachable cap and the pressure sensor port further adapted to detect a second ambient pressure outside the cap, and wherein every time the cap is turned on, the controller is further programmed to calibrate the pressure sensor by calculating a zero flow rate through the detachable cap based on a pressure differential reading between the second detected ambient pressure at the pressure sensor port and the second internal air pressure within the detachable cap.

8. The detachable cap of claim 1, further comprising a capacitive touch sensor in the roof portion of the cap, the capacitive touch sensor being communicatively coupled to the controller and adapted to detect a touch of a user, wherein the controller is configured to differentiate between an accidental touch by the user and an intentional inhaler use by the user, wherein the differentiation is determined by detecting:
a touch duration value by the capacitive touch sensor,
a force sensor value by a force sensor, the force sensor being communicatively coupled to the controller and adapted to detect a user force applied to the roof portion of the detachable cap,
an orientation information from an accelerometer, the accelerometer being communicatively coupled to the controller and adapted to detect an orientation of the inhaler, and
one or more flow values from the pressure sensor, and
comparing the detected touch duration value, a detected force sensor value, a detected orientation information, and one or more flow values with a predetermined touch duration value, a predetermined force sensor value, a predetermined orientation information, and one or more predetermined flow values stored in an on-board memory that are indicative of an accidental touch,
wherein, the controller is configured to turn off the cap in response to determining that the touch of the user is an accidental touch.

9. A method of detecting usage of an inhaler, comprising:
providing a detachable cap adapted to removably receive the inhaler, the detachable cap comprising:
a hollow receiving portion configured to snugly fit an outer body of the inhaler, wherein the receiving portion further comprises a rigid roof portion;
a vent, formed in the roof portion of the detachable cap and located above a plane defined by a top surface of a canister located in the inhaler, to allow a flow of inhaled air through the detachable cap to the inhaler, the vent defined by a fixed size opening through the roof portion, wherein a height of the cap and the size of the vent are configured to facilitate laminar air flow through the cap and vent, and configured to create a constant resistance to the flow of inhaled air during use of the inhaler;
an electronic circuit having a controller coupled to a storage device and a power source,
a pressure sensor inside the detachable cap, underneath the roof portion, and adjacent to the vent, wherein the pressure sensor comprises a pressure sensor port situated on the outside of the detachable cap, the pressure sensor communicatively coupled to the controller and adapted to detect a first internal air pressure within the detachable cap, underneath the roof portion, and adjacent to the vent, and the pressure sensor port adapted to detect a first ambient pressure outside the cap;

switching on and switching off the detachable cap automatically based on the pressure sensor, a force sensor and an accelerometer;

detecting the first internal air pressure within the detachable cap, underneath the roof portion, and adjacent to the vent, and detecting the first ambient pressure outside the cap;

calculating, with the controller, an inhaled air flow rate through the detachable cap based on the difference between the first detected ambient pressure and the first detected internal air pressure based on Bernoulli's principle; and storing the calculated air flow rate in the storage device.

10. The method of claim 9, further comprising:

detecting a user force applied to the roof portion of the detachable cap with the force sensor provided in the roof portion and communicatively coupled to the controller; and calculating, with the controller, the air flow rate through the detachable cap when the user force applied to the roof portion of the detachable cap is detected.

11. The method of claim 9, further comprising:

detecting an orientation of the inhaler with the accelerometer;

determining whether the inhaler has been shaken with at least one of the accelerometer and the pressure sensor;

storing the detected orientation of the inhaler and the determination of whether the inhaler has been shaken in the storage device; and providing a notification to a user to shake the inhaler when the detachable cap is subjected to the user force and the inhaler has not been shaken.

12. The method of claim 11, further comprising:

applying a timestamp with a timer corresponding to usage of the inhaler;

storing actual parameters of inhaler usage as a function of time in the storage device, the parameters including the calculated air flow rate, the user force, the detected orientation of the inhaler, the determination of whether the inhaler has been shaken, and the applied timestamp;

storing in the storage device a predetermined range of parameters that define recommended inhaler usage;

comparing the actual parameters of inhaler usage with the predetermined range of parameters; and determining whether the inhaler usage is recommended inhaler usage.

13. The method of claim 12, further comprising:

providing a notification to the user related to whether the inhaler usage is recommended inhaler usage, the notification being in the form of audio cues through a speaker in the detachable cap, visual cues through a light emitting diode in the detachable cap, or haptic cues through a haptic motor in the detachable cap, and the notification being provided while the inhaler is being used for medication delivery or after completion of medication delivery.

14. The method of claim 9, wherein the receiving portion further comprises a rigid side surface.

15. The method of claim 9, further comprising:

calibrating the pressure sensor by calculating, with the controller every time the cap is turned on, a zero flow rate through the detachable cap based on a pressure differential reading between a second detected ambient pressure at the pressure sensor port and a second internal air pressure within the detachable cap, the pressure sensor further adapted to detect the second internal air pressure within the detachable cap and the pressure sensor port further adapted to detect the second ambient pressure outside the cap.

16. The method of claim 9, further comprising:

switching on and switching off the detachable cap automatically based on a capacitive touch sensor, the detachable cap further comprising the capacitive touch sensor in the roof portion of the cap, the capacitive touch sensor being communicatively coupled to the controller and adapted to detect a touch of a user, wherein the controller is configured to differentiate between an accidental touch by the user and an intentional inhaler use by the user, wherein the differentiation is determined by detecting:

a touch duration value by the capacitive touch sensor, a force sensor value by the force sensor, the force sensor being communicatively coupled to the controller and adapted to detect a user force applied to the roof portion of the detachable cap, an orientation information from the accelerometer, the accelerometer being communicatively coupled to the controller and adapted to detect an orientation of the inhaler, and one or more flow values from the pressure sensor, and comparing the detected touch duration value, a detected force sensor value, a detected orientation information, and one or more flow values with a predetermined touch duration value, a predetermined force sensor value, a predetermined orientation information, and one or more predetermined flow values stored in an on-board memory that are indicative of an accidental touch, wherein, the controller is configured to turn off the cap in response to determining that the touch of the user is an accidental touch.

17. An inhaler, comprising: an inhaler body; and a detachable inhaler cap for measuring usage of the inhaler, the detachable cap comprising:

a hollow receiving portion adapted to removably receive the inhaler body and configured to snugly fit an outer body of the inhaler, wherein the receiving portion further comprises a rigid roof portion;

a vent, formed in the roof portion of the detachable cap and located above a plane defined by a top surface of a canister located in the inhaler, to allow a flow of inhaled air through the detachable cap to the inhaler body, the vent defined by a fixed size opening through the roof portion, wherein a height of the cap and the size of the vent are configured to facilitate laminar air flow through the cap and vent, and configured to create a constant resistance to the flow of inhaled air during use of the inhaler;

an electronic circuit including a controller coupled to a storage device and a power source;

a pressure sensor inside the detachable cap, underneath the roof portion, and adjacent to the vent, wherein the pressure sensor comprises a pressure sensor port situated on the outside of the detachable cap, the pressure sensor communicatively coupled to the controller and adapted to detect a first internal air pressure within the detachable inhaler cap, underneath the roof portion, and adjacent to the vent and the pressure sensor port adapted to detect a first ambient pressure outside the cap, wherein the controller is programmed to calculate an inhaled air flow rate through the detachable cap based on the difference between the first detected ambient pressure and the first detected internal air pressure based on Bernoulli's principle and to store the calculated air flow rate in the storage device.

18. The detachable cap of claim 1, wherein the receiving portion further comprises a rigid side surface.

19. The detachable cap of claim 1, wherein the pressure sensor is further adapted to detect a second internal air pressure within the detachable cap and the pressure sensor port further adapted to detect a second ambient pressure outside the cap, and wherein every time the cap is turned on, the controller is further programmed to calibrate the pressure sensor by calculating a zero flow rate through the detachable cap based on a pressure differential reading between the second detected ambient pressure at the pressure sensor port and the second internal air pressure within the detachable cap.

20. The detachable cap of claim 1, further comprising a capacitive touch sensor in the roof portion of the cap, the capacitive touch sensor being communicatively coupled to the controller and adapted to detect a touch of a user,
    wherein the controller is configured to differentiate between an accidental touch by the user and an intentional inhaler use by the user, wherein the differentiation is determined by detecting:
    a touch duration value by the capacitive touch sensor,
    a force sensor value by a force sensor, the force sensor being communicatively coupled to the controller and adapted to detect a user force applied to the roof portion of the detachable cap,
    an orientation information from an accelerometer, the accelerometer being communicatively coupled to the controller and adapted to detect an orientation of the inhaler, and
    one or more flow values from the pressure sensor, and
    comparing the detected touch duration value, a detected force sensor value, a detected orientation information, and one or more flow values with a predetermined touch duration value, a predetermined force sensor value, a predetermined orientation information, and one or more predetermined flow values stored in an on-board memory that are indicative of an accidental touch,
    wherein, the controller is configured to turn off the cap in response to determining that the touch of the user is an accidental touch.

\* \* \* \* \*